US007012547B2

(12) United States Patent
Hassett

(10) Patent No.: US 7,012,547 B2
(45) Date of Patent: *Mar. 14, 2006

(54) ELECTRONIC VEHICLE TOLL COLLECTION SYSTEM AND METHOD

(75) Inventor: John J. Hassett, Marblehead, MA (US)

(73) Assignee: Transcore, Inc., San Diego, CA (US)

( * ) Notice: Subject to any disclaimer, the term of this patent is extended or adjusted under 35 U.S.C. 154(b) by 13 days.

This patent is subject to a terminal disclaimer.

(21) Appl. No.: 10/219,880

(22) Filed: Aug. 15, 2002

(65) Prior Publication Data

US 2003/0067396 A1    Apr. 10, 2003

Related U.S. Application Data

(63) Continuation-in-part of application No. 09/140,778, filed on Aug. 27, 1998, now Pat. No. 6,653,946, and a continuation-in-part of application No. 07/945,534, filed on Sep. 16, 1992, now Pat. No. 5,347,274, which is a continuation-in-part of application No. 07/901,277, filed on Jun. 19, 1992, now Pat. No. 5,406,275, which is a continuation-in-part of application No. 07/901,278, filed on Jun. 19, 1992, now Pat. No. 5,289,183, which is a continuation-in-part of application No. 07/525,103, filed on May 17, 1990, now Pat. No. 5,144,553.

(51) Int. Cl.
*G08G 1/065* (2006.01)
(52) U.S. Cl. .................. 340/928; 340/539.13; 342/457
(58) Field of Classification Search ................ 340/928, 340/991, 988, 426.19, 539.11, 539.13, 539.15, 340/539.1; 701/219, 300, 207; 342/457
See application file for complete search history.

(56) References Cited

U.S. PATENT DOCUMENTS

| | | | | |
|---|---|---|---|---|
| 3,697,941 A | * | 10/1972 | Christ | 340/991 |
| 3,757,290 A | * | 9/1973 | Ross et al. | 340/991 |
| 4,217,588 A | * | 8/1980 | Freeny, Jr. | 342/458 |
| 5,187,810 A | * | 2/1993 | Yoneyama et al. | 455/509 |
| 5,208,756 A | * | 5/1993 | Song | 455/456.3 |
| 6,653,946 B1 | * | 11/2003 | Hassett | 340/928 |

OTHER PUBLICATIONS

Evans, Stuart M., et al., IBTTA AVI Conference Proceedings, Jun. 1990, New York, New York.

* cited by examiner

*Primary Examiner*—Brent A. Swarthout
(74) *Attorney, Agent, or Firm*—Foley & Lardner LLP

(57) ABSTRACT

A system for automatic collection of tolls includes an in-vehicle toll processor having memory for storing a toll-money-available quantity purchased by the user, and a toll-facility-identification site that transmits a toll-facility-identifier signal indicating the identity of the upcoming toll facility. As the vehicle approaches the identification site, the in-vehicle processor receives the identifier signal and calculates the toll to be debited. When the vehicle passes through the toll facility, the in-vehicle processor transmits its identity, its net balance and the toll, which it debits from an account balance. The in-vehicle processor may increment a low balance, in which case it transmits information which is relayed to a central system for billing. Various means for shutting down delinquent in-vehicle components or identifying offender vehicles are described.

4 Claims, 14 Drawing Sheets

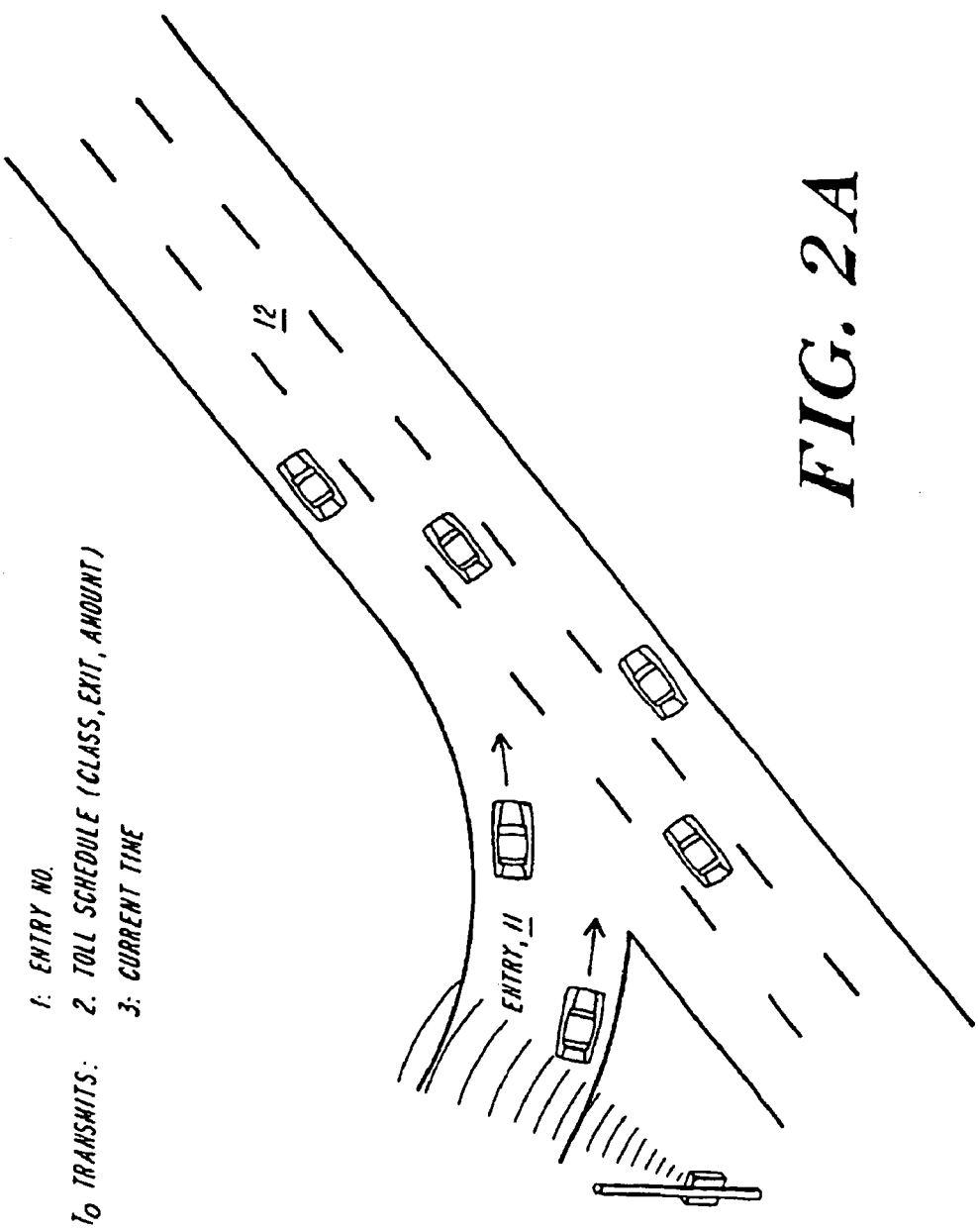

ELECTRONIC VEHICLE TOLL COLLECTION SYSTEM AND METHOD

This patent application is a continuation-in-part of U.S. Ser. No. 09/140,778, filed Aug. 27, 1998, now U.S. Pat. No. 6,653,946, which is a CIP of U.S. Ser. No. 07/901,277, filed Jun. 19, 1992, now U.S. Pat. No. 5,406,275, which is a CIP of U.S. Ser. No. 07/525,103, filed May 17, 1990, now U.S. Pat. No. 5,144,553, and is a CIP of U.S. Ser. No. 07/945,534, filed Sep. 16, 1992, now U.S. Pat. No. 5,347,274, which is a CIP of U.S. Ser. No. 07/901,278, filed Jun. 19, 1992, now U.S. Pat. No. 5,289,183. Each of the foregoing patents and patent applications is hereby incorporated by reference herein in its entirety.

Each of the foregoing patents and patent applications generally discloses systems wherein a mobile vehicle transponder unit is associated with a vehicle and communicates with one or more fixed transceiver units at one or more locations, exchanging and updating individual status information, as the vehicle moves. The information is generally account information, although in the case of Ser. No. 945,534 this is primarily vehicle-specific load status, measurement, route or other evolving information. In the present invention, the information is debit account toll information, and communications between the vehicle transponder, also referred to as an in-vehicle component or "IVC," occur at or near the toll collection stations located along a route.

BACKGROUND OF THE INVENTION

This invention relates generally to systems for vehicle toll collection, and, more particularly, relates to apparatus and methods for automatic, non-contact, high-speed collection of vehicular tolls.

An increasing number of vehicles are traveling over progressively more congested highways. The collection of tolls by conventional means has had a negative effect upon highway throughput and safety. Congestion and long backups on toll plazas are becoming more common. Such conditions involve a significant economic cost, through lost time, and reduced productivity. Moreover, serious accidents at toll plazas, caused by operator or mechanical failure, have also increased in frequency.

Certain toll authorities have attempted to respond to these problems by providing coin-operated toll collection devices, or by instituting a toll-plate system in which toll-takers visually inspect each incoming vehicle for an appropriate toll plate or sticker. Coin-operated toll collection systems, however, do little to increase throughput, and are susceptible to fraud, through the use of counterfeit coins. Toll-plate systems suffer the same deficiencies, requiring each vehicle to slow sharply while entering the visual inspection area; these systems also rely heavily on toll-taker attentiveness.

Additionally, a number of systems have been proposed for utilizing radio frequency identification (RFID) techniques for toll collection. Under these systems, drivers acquire a "tag" or card that acts as a reflective transmitter or discrete transmitter to identify the vehicle by serial number as it passes through a toll booth. This technique is also referred to as Automatic Vehicle Identification (AVI).

This system also suffers from a number of deficiencies. In particular, because the RFID tag lacks a machine-intelligent processor for manipulation and storage of accounts, toll authorities must maintain individual toll accounts for all users of the system. This becomes especially burdensome in urban areas or regions of high toll traffic volume. Toll agencies would need to manage hundreds of thousands of individual accounts, a burden that is created by operation of the AVI system.

Additionally, because the RFID tags lack a processor or user interface, vehicle operators cannot readily ascertain account balances, and have no warning as to limited or exhausted credit. This creates both confusion, and potential safety hazards, as drivers cross over to conventional toll collection lanes with little warning.

Further, in the absence of a single national toll agency, each participating driver would need to have multiple cards attached to the vehicle, each corresponding to a separate toll authority account.

The RFID system also raises user-privacy issues by requiring the generation and storage of detailed vehicle-specific travel records.

In response to the inability of conventional toll collection means to meet the demands created by increased highway traffic, automated toll facilities that provide improved toll collection methods and systems have been proposed. These automated toll facilities eliminate the manual transactions of conventional toll collection means through the use of radio transmitters and receivers that perform the necessary transactions as a vehicle travels through the automated toll booth. One such system electronically collects tolls from an electronic cache of toll credits carried within the vehicle. In this way, a vehicle operator can purchase a quantity of toll credits prior to traveling on a toll road. As the vehicle later travels through a toll collection booth, a radio-frequency exchange occurs and the appropriate amount is automatically debited from the vehicle's toll credits.

Although the automated toll collection system described above functions well for single lane toll roads or single lane bridges and tunnels, a significant problem can exist when the system is practiced in a multi-lane environment. In a multi-lane environment, each toll lane is equipped with a stationary radio-transceiver to interact with the mobile radio-transceiver of vehicles passing through that lane. The problem of multi-pathing occurs when information transmitted from a vehicle in one lane is picked up by multiple toll lane stationary transceivers. Therefore the possibility exists that a toll collected from a vehicle in lane 1 may be credited to the vehicle in lane 2. The effect of multi-pathing allows toll-evaders to exploit automated toll systems, as well as accidentally misallocating the debits.

A number of prior art systems exist that minimize the effects of multi-pathing. These systems typically attempt to shield the toll transceiver of one lane from signals transmitted from mobile units traveling in an adjacent lane. Such systems include methods that establish a proximity zone that identifies when a vehicle has entered a predetermined region, and then requires the vehicle to transmit the toll within a predetermined time limit. Other systems establish a multi-field environment, where a blanking field is transmitted behind and adjacent to a region proximate to the toll lane. The blanking zone serves to swamp out any multi-path signals that could be received by the toll station. The prior art systems do not provide a means for determining the actual lane position of an oncoming mobile unit. Because of this, the prior art systems do not allow the toll system to determine the physical sequence of oncoming traffic approaching the toll system. Moreover, the prior art systems place constraints on the size of the lanes and the spacing that must exist between each lane transceiver.

It is accordingly an object of the invention to provide improved toll collection methods and apparatus that significantly increase the traffic capacity of roadways.

Another object of the invention is to provide toll collection methods and apparatus that increase the rate of toll collection while enhancing highway safety.

A further object of the invention is to provide such methods and apparatus that are convenient to use and support toll collection by a plurality of toll authorities or authorities at a plurality of widely separated locations.

Yet another object of the invention is to provide toll collection systems that reduce administrative burdens, facilitate the generation of transaction reports for users and toll authorities, and preserve the privacy of users.

It is a further object of the invention to provide toll collection systems that are reliable and resistant to attempts at fraud or toll evasion, and which are readily integrated into existing toll management systems.

Another object of the present invention is to provide a system for determining the lane position of a vehicle approaching an automated toll system.

A further object of the invention is to provide a mechanism for determining the sequence of mobile units approaching an automated toll system.

An additional object of the invention is to provide a system for determining the relative position of a mobile object approaching a stationary transceiver.

And yet another object of the invention is to provide a system for automatic toll collection that uses toll transceivers that can work in close proximity with other toll transceivers.

Other general and specific objects of the invention will in part be obvious and will in part appear hereinafter.

SUMMARY OF THE INVENTION

The foregoing objects are attained by the invention, which provides methods and systems for automatically collecting tolls from a vehicle moving at high speed along a roadway.

One aspect of the invention includes at least a first toll facility through which the vehicle can pass for toll collection, and an in-vehicle transponding toll processor having storage for storing a toll-money-available signal representative of a monetary quantity available for debiting in a toll transaction at an upcoming toll facility and a vehicle-specific identifier. Initially, the toll processor is loaded, for example, at a toll facility, with an electronic gross-toll-amount signal representative of an initial toll-money-available value.

A first toll-facility-identification site, corresponding to and remote from a first toll facility collection site, transmits a first toll-facility-identifier signal uniquely representative of (i) the location of the first toll facility and optionally also (ii) a toll schedule corresponding to the roadway. As the moving vehicle approaches the first toll-facility-identification site, the in-vehicle toll processor receives and stores the first toll-facility-identifier signal, and calculates, in response to the first toll-facility-identifier signal, a toll amount to be debited at the first toll facility.

In particular, the in-vehicle toll processor compares the calculated toll amount with the toll-money-available signal stored in the in-vehicle processor, to test whether the monetary quantity represented by the toll-money-available signal is greater than or equal to the calculated toll amount. The in-vehicle toll processor preferably responds to a selected result of this comparison by providing the vehicle operator with a signal, such as a beep, or a beep accompanied by a flashing colored light, representative of permission to utilize the first automated toll facility.

Subsequently, as the vehicle approaches and passes through the first toll facility collection site, the first toll facility collection site transmits a toll-collect signal instructing the in-vehicle toll processor to debit the toll amount from its storage. The in-vehicle toll processor responds by debiting the calculated toll amount from its storage, reducing the value of the toll-money-available signal in accordance with the amount debited. Additionally, the in-vehicle toll processor transmits transaction acknowledgment signal indicating to the toll facility collection-site its identification, the calculated toll amount and the account balance.

In another aspect of the invention, when the comparison executed by the in-vehicle toll processor indicates that the toll money available is less than the calculated toll amount, or is less than a preselected programmed minimum balance, such as twenty dollars, the in-vehicle toll processor responds by internally incrementing the balance, and activating a debit message to assure that the toll facility charges the new increment to a credit or billing agency, such as a bank account or credit card company.

A further aspect of the invention provides for operation on a progressive toll roadway, on which toll amounts depend upon where the vehicle enters and where it exits the tollway. In this aspect the invention includes at least a second toll facility remote from the first toll facility, with a second toll-facility-identification site corresponding to and remote from a second toll facility collection site. The second toll-facility-identification site transmits at least a second toll-facility-identifier signal uniquely representative of (i) the location of the second toll facility and preferably also (ii) the toll schedule corresponding to the roadway. As discussed further below, the toll schedule may be the schedule for all classes of vehicles for all exits, or may be the schedule for all vehicles entering or exiting at the particular site.

The in-vehicle toll processor receives the second toll-facility-identifier signal, and if the vehicle did not previously pass through the first toll collection facility. the in-vehicle toll processor overwrites the stored first toll-facility-identifier signal with the second toll-facility-identifier signal.

In one aspect of the invention, the toll-facility-identifier signals, the vehicle identifier and toll-transaction signals or acknowledgment signals are encoded radio-frequency signals, and the encoding can be dynamically varied to reduce the possibility of fraud, or to carry additional selected information.

Precise identification of the position of a vehicle as it passes a toll station is achieved in one aspect of the invention, which includes at least one stationary transceiver unit positioned above one lane of a multi-lane roadway that transmits an identification signal in a known field pattern. A mobile transceiver unit traveling along the multi-lane roadway receives the identification signal and decodes the identity of the stationery transceiver unit and evaluates the strength of the signal. From this information, the mobile transceiver determines its position with respect to the stationery transceiver unit.

In particular, at least one stationery transceiver unit is positioned above one lane of a multi-lane roadway. The transceiver includes a highly directional antenna that transmits a radio-frequency signal. The signal is directed along the roadway and in the direction of oncoming traffic. The directional signal broadcast from the antenna sets up a field pattern within one lane of the multi-lane roadway. By encoding the signal with information that identifies the lane in which the antenna is directed, a radio-frequency field can be set up that uniquely identifies one lane of the roadway.

A vehicle equipped with a transceiver made in accordance with the present invention can determine its lane of travel and its distance from the stationery transceiver by receiving and processing the antenna field pattern. The mobile transceiver, fixed within a vehicle such as an automobile, receives signals generated by the stationery transceivers. The mobile transceiver then decodes these signals and determines from which lane the signal was broadcast. The mobile transceiver then associates with each lane identity a signal strength that can be compared to the known field pattern of the stationery transceiver directional antenna. The mobile transceiver processes the signal strength and signal identity and determines its location relative to the stationery transceiver.

Subsequently, as the vehicle passes the stationery transceiver units, it transmits its vehicle identification number and its lane position so that the stationery transceivers know which vehicle is passing in which lane.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a more complete understanding of the nature and objects of the invention, reference should be made to the following detailed description and the accompanying drawings, in which:

FIG. 2A indicates an alternative embodiment;

DESCRIPTION OF ILLUSTRATED EMBODIMENTS

The invention involves a bidirectional module in each vehicle for reception, storage and computation, and transmission of information, wherein the modules communicate with RF transceivers at a toll station, preferably configured to identify toll lanes. While all communications can occur while vehicles are traveling at highway speeds, the location of each vehicle is known with precision, allowing effective enforcement against scofflaws and toll offenders. The traffic lane localization technology will be understood by skipping briefly ahead to FIG. 11.

Figure 11:
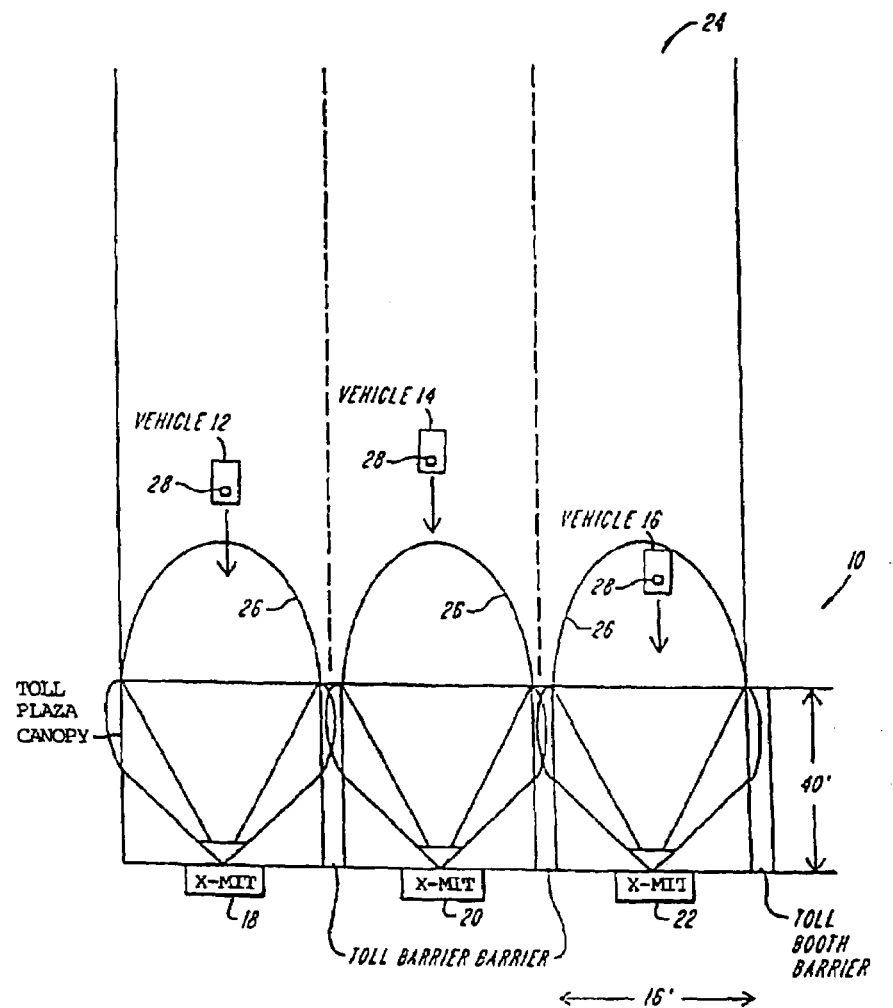
FIG. 11 shows a schematic block diagram of a roadway traffic monitoring and management system according to the invention.

FIG. 11 shows a block diagram of a multi-lane vehicle location system 210 according to the invention. The illustrated embodiment 210 enables vehicle position to be determined and transferred from vehicle transponders, located in host vehicles 212–216, to the lane transmitter units 218–222, as the vehicles 212–216 travel along the roadway 224.

For simplicity, FIG. 11 depicts a three-lane road 224 on which the direction of travel for a given host vehicle, referred to herein as the "downstream" direction, is indicated by arrows. Those skilled in the art will appreciate that the invention can be practiced in connection with roadways having additional-lanes, including multi-lane divided highways, bridges and tunnels. As one skilled in the art will appreciate the invention can also be practiced in connection with numerous other transport systems, such as railways, and waterways.

The illustrated embodiment includes two primary components; the vehicle transponders 28, and the lane stationary transceivers 218–222. As discussed in further detail below, a vehicle transponder 228, according to a preferred embodiment, is carried by a host vehicle and includes a radio frequency transmitter and receiver, a central processing unit, an early warning signal detection unit, a signal strength detection unit, a signal decoding unit, and a user interface. The preferred embodiment of the roadway stationary transceiver includes a transmitter unit and a directional antenna having a known antenna pattern directed at the lane below the transmitter unit.

The vehicle transponder 228 receives signals from the lane transmitter units 218–222 and processes these signals to determine which lane stationary transmitter unit sent a particular signal. The transponder 228 may also process the signals to determine the relative strengths of the signals received from the various lane transmitting units. By comparing the measured and strengths of the received signals and comparing this information to known antenna field strength patterns, the transponders can determine their lane position and accordingly the vehicle position relative to the lane transmitting units.

In the embodiment of the present invention illustrated in FIG. 11, the lane transmitting units 218–222 are positioned across the multi-lane roadway so that one transmitting unit is positioned above each lane. As further indicated by FIG. 11, each of transceivers unit 218 through 222 radiates a lane identification signal that establishes an antenna field pattern 226 in the direction of on-coming traffic. The lane identification signal is encoded with lane identification information so that a single field pattern is associated with a particular lane. In the illustrated embodiment, the signal generated by transceivers units 218–222 is a radio-frequency (RF) signal.

Figure 12:
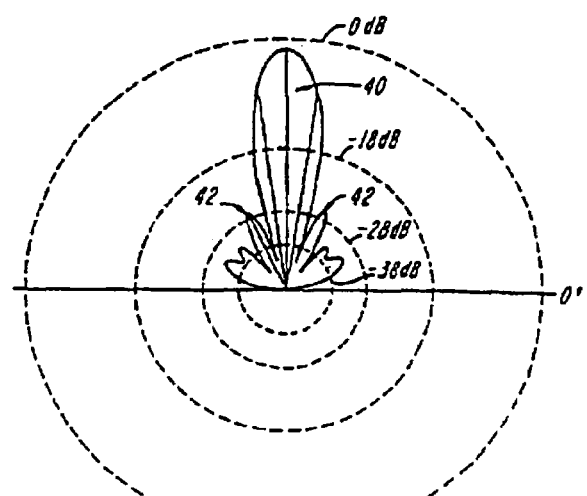
FIG. 12. is a graphical depiction of the antenna field pattern plotted in polar coordinates.

FIG. 12 illustrates in more detail the antenna pattern radiated from the transmitting units of transceivers 218–222. In the example illustrated in FIG. 12, the field pattern is established by a phased array radar system with parasitic directors transmitting at 904.5 Mhz, but it should be apparent that any similar transmitting device known in the art could be used. More specifically, the antenna field pattern was generated by a slotted waveguide array with longitudinal polarization in the direction of travel and beam shaping. The phased array antenna transmits the majority of its radiated energy within the main lobe 240. As is known in the art, the side lobes 242 are minimized to prevent false target detection. As shown in FIG. 12, the side lobes are attenuated approximately 18 db from the main lobe and extend at approximately 225 degree angles. By radiating such known field patterns along each lane of the roadway, the roadway is effectively divided into separate radiation field regions.

It should be apparent to those skilled in the art that in an alternative embodiment of the invention, a back lobe projected from the rear of the antenna, is used to create larger region of known field pattern.

Figure 13:
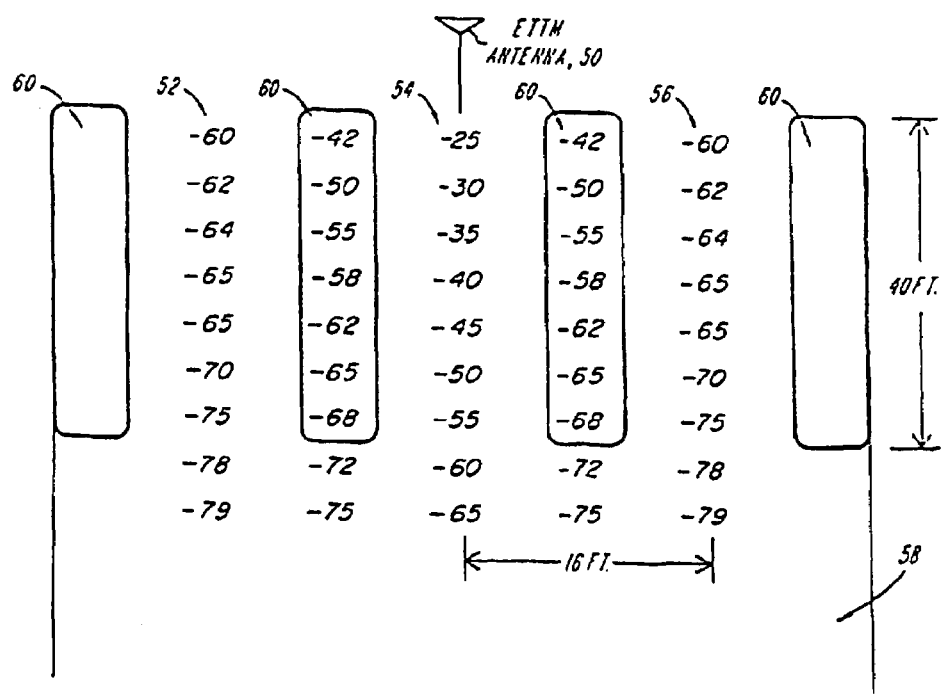
FIG. 13 is a graphical diagram of one embodiment of the present invention illustrating the pattern of radio field energy established by an antenna.

FIG. 13 illustrates an example of the roadway being divided into known regions by antenna patterns. In FIG. 13, an antenna element 250 radiates a known field activity pattern along three lanes 252, 254, and 256 of a roadway 258. In the illustrated embodiment, each lane of the roadway is separated by a toll barrier 260. The numerical values in each lane or at each barrier, e.g. (−25) represent the decrease in intensity level of the RF field at each location expressed in db. In the example shown, a signal directed along the center lane 254 establishes an energy gradient that relates to the distance from the antenna element 250. In the illustrated example, the antenna field strength in lane 254 decreases 30 db over the forty feet measured from one end of the toll barrier 260 to the far end. As further shown in FIG. 13, parallel positions within the adjacent lanes 252 and 256 are a minimum of 14 db below a parallel point in the center lane 254, (i.e., −65 db for the center lane and −79 db for the adjacent lanes). As a mobile transceiver approaches antenna 250, the intensity difference between parallel positions within adjacent lanes increases (i.e. a 45 db difference at the point closest to the antenna). In the example shown, the center of each lane is separated from the center of the adjacent lane by a minimum of 14 feet. In this way, the present invention allows transceiver units 218–222 to be spaced apart the typical separation of a conventional toll booth.

As can be seen from the example shown in FIG. 13, a signal strength measurement of −40 db, corresponds to the region of the roadway that is about halfway along defined lane 254. Those skilled in the art will appreciate that the invention can be practiced with other field strength patterns that indicate a position relative to a transmitting unit. Those skilled in the art will further appreciate that the field pattern can be generated by an intermittent or constant transmission or that each field can have independent frequency characteristics.

In one practice of the invention, lane identification information is digitally encoded into the signal broadcast from the transmitting units. For digitally encoded information, data fields are created that establish header information and data information:

| Field | Size |
|---|---|
| Start File | 2 bytes |
| Lane Identification | 4 bits |
| End File | 2 bytes |

Those skilled in the art will appreciate that the invention can be practiced in connection with other data field parameters or alternative forms of encoding techniques, such as phase shift keying, manchester encoding or other techniques know in the art.

FIG. 14 depicts detail of the transponder 228. The transponder includes a data processor 270, a signal receiver 272, connected to an antenna element 273, a decoding means 274, connected to the signal receiver 272, a signal strength detection unit 276, connected between receiver 272 and processor 270, an early warning signal detection unit 278 also connected between receiver 272 and processor 270, a transmitter 280, a memory element 288 is connected to processor 270, and a user interface section 283. A conventional power supply 289 provides the power requirements of the transponder.

The processor 270 can be an 8086 microprocessor or an 8051 microcontroller, or other processor capable of executing the calculations necessary to determine vehicle position. In the embodiment depicted in FIG. 14A, decoding means 274, connected to receiver element 272 and processor element 270, decodes the lane identification information encoded in the signal received at receiver 272. In an alternative embodiment, the processor 270 also decodes and interprets the encoded signals in a manner described in greater detail hereinafter. The memory element 288, preferably provides sufficient non-volatile memory to store program information including information for processing of signal strength detection information and lane identification information.

The transponder antenna 273, can be incorporated into the transponder module itself or a receptacle can be provided to attach to a conventional window mounted antenna, similar to those employed in connection with cellular telephone devices.

The user interface section 283 preferably include user operable keys 282, LCD or LED display unit 284, and a audio alarm module 286. The display and audio alarm elements provide visual, audible alarm signals when necessary, while the keys and display elements enable the vehicle operator to obtain information relating to lane position and distance from stationary base units, as well as enter any information that may be required. The display and user interface keys, in combination with conventional stored software routines controlling the processor, enable the user to view information concerning the vehicles position within a lane or along the roadway. In one embodiment, the user interface includes an alpha numeric display having two lines of ten characters each.

Power supply elements preferably include a compact user replaceable long-life battery 289, such as a lithium power cell. These elements can also include an on/off switch incorporating a battery check position.

Figure 14A:
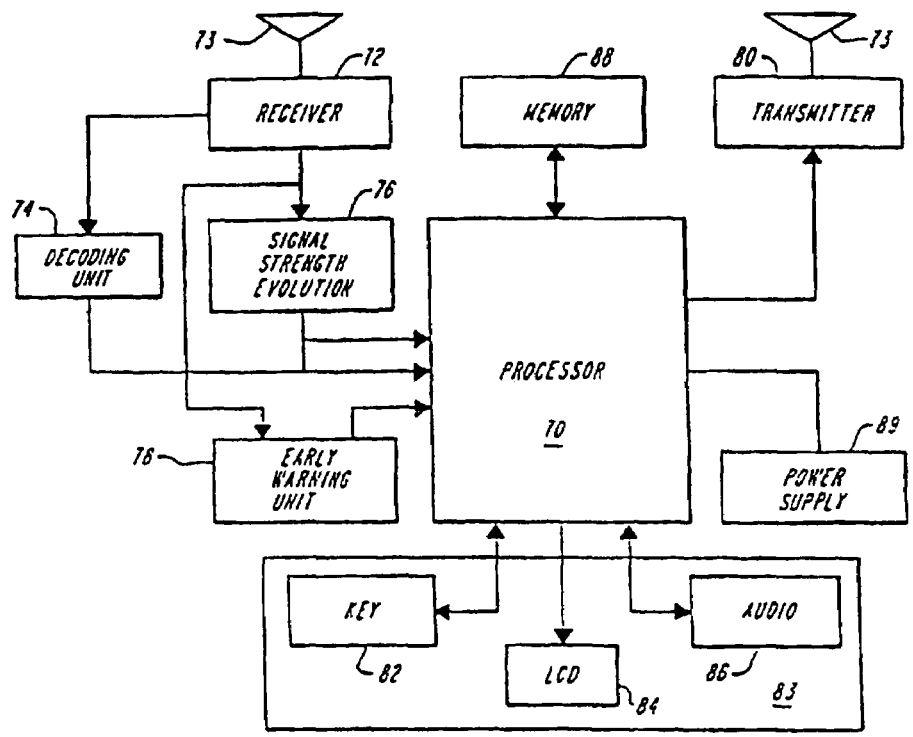
FIG. 14 is a schematic block diagram of a vehicle transponder, particularly adapted for operation in the system of FIG. 11.

The components depicted in FIG. 14A are conventional in design and construction, and the transponder can be constructed in accord with known transponder and microprocessor principles. The illustrated transponder can be housed in a compact portable enclosure adapted for removable attachment to a dashboard surface or other convenient location within a vehicle.

The combination of components depicted in the FIG. 14A enables the transponder to process signal information and determine its lane position and linear distance from a stationery transmitting unit. Furthermore, the transponder memory 288 can store software and algorithms for determining the position of the moving vehicle relative to the positions of the other lanes on the roadway. As will be described in greater detail hereinafter, the relative position of vehicles traveling along a multilane roadway can be transmitted to an automated toll system or other automated traffic management system to determine the sequence of traveling traffic moving along a multilane roadway.

In one embodiment of the invention the microprocessor has a low power consumption state, a standby mode, that is used to conserve power. In standby mode the microprocessor halts all activity. The processor is brought out of this mode by activating an input on the microprocessor 270. Conserving power when the transponder is not processing signal position information, reduces average power demands and significantly extends battery life.

Figure 14B:
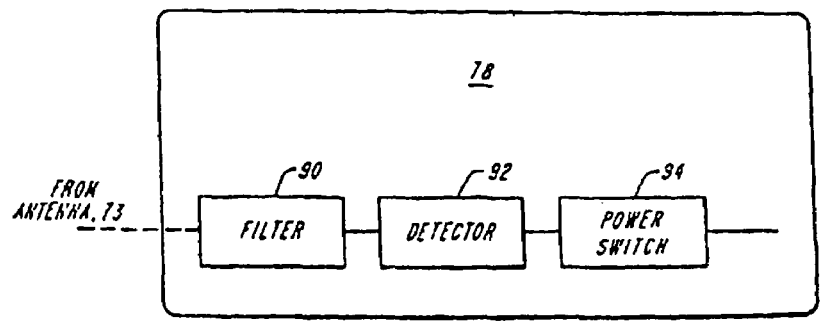

FIG. 14B, depicts the components of an early warning unit as practiced in one embodiment of the invention. The function of the early warning unit is to "wake up" the remainder of the transponder circuit via power switch 294. Filter 90 monitors signals picked up by antenna 273. Filter element 290 is a typical bandpass filter constructed as known in the art and functions to detect specific frequencies within the electromagnetic spectrum. Signals passed from filter 290 are sent to detector element 292 that is constructed from a diode and capacitor array or any other construction known in the art. The detector functions to determine the signal strength of the filtered signal. If the filtered signal has sufficient energy then the detector determines the vehicle to be approaching an antenna field pattern. The detector unit 292 relays a signal to power switch 294. Power switch 294 activates the microprocessor 270.

The signal strength detection unit 276 receives the signal from the receiver unit 272. The signal strength detection unit 276 measures the strength of the received analog signal and performs an analog to digital conversion to generate a digital signal indicative of the signal strength. The digital signal is transferred to the processor 270 for determining the position of the vehicle as will be explained in greater detail hereinafter.

The signal decoding means 274 processes signals sent from receiver unit 272 and decodes the lane identification information transmitted with the signal. The lane identification information is sent to the processor means 270. Processor means 270 tags the measured signal strength with the lane identification signal. The processor then uses the lane identification information and the signal strength information to determine position of the vehicle relative to the transmitting units.

In an alternative embodiment, the carrier is removed from the lane identification information signal and the data is left. The lane identity and error correction information is decoded from a manchester encoded format and checked for errors. Other forms of error correction known in the art can be used to check the integrity of the received signal.

Figure 15:
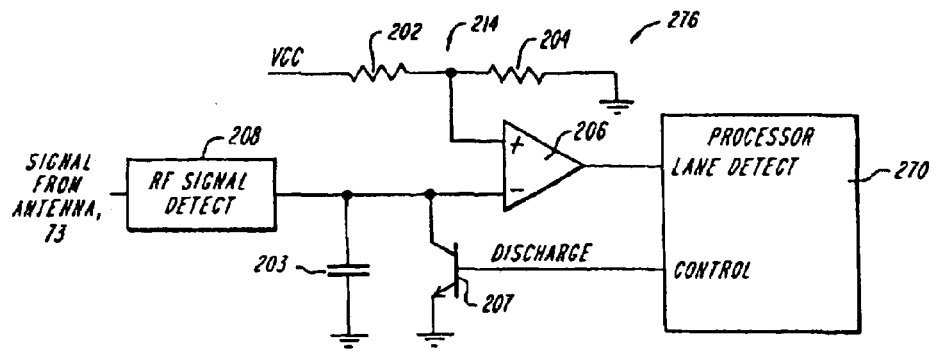
FIG. 15 is a schematic block diagram in accord with one embodiment of the invention for determining the linear distance from a roadway traffic transceiver.

FIG. 15 illustrates one example of the circuit design for the signal strength detection unit 276. The example depicted in FIG. 15 is illustrative of one possible construction of a signal strength detection unit that achieves economy, and therefore promotes the use of the present invention.

A signal received by antenna 273 is sent to unit 276. Signal strength detection unit 276 has a storage capacitor 203 of known value so that capacitor 203 charges at a known rate as the signal from receiver 272 is transferred to the capacitor 203. Unit 276 has a comparator element 206 having its inverting input connected to storage capacitor 203. The non-inverting input of comparator element 206 is connected to a bias element 214. The bias element depicted is a simple voltage divider constructed from two resistors 202 and 204. The voltage across resistor element 204 is a constant reference voltage.

The output of the comparator element 206 is connected to a lane detect input pin on the processor element 270. A high state on the lane detect pin indicates that the voltage across capacitor 203 is greater than the reference voltage across resistor 204. The processor element 270 has an output pin connected to the base input of discharge transistor 207. The collector of discharge transistor 207 is connected to the inverting input of the comparator 206 and the signal input of the storage capacitor 203. The processor can reset the storage capacitor 203 by activating the transistor element 207 through its output control pin.

The configuration of elements in FIG. 15 forms a one bit analog to digital converter that can sample an incoming signal for a specific period of time and compare the collected voltage to a known reference signal. Once the signal is read, the converter is reset, by removing the stored voltage across capacitor 203, and the process runs again. In this way the capacitor 203 and comparator 206 and biasing network 214 form a one bit analog to digital converter that generates a digital signal indicative of the strength of the received signal. The ratio of resistor elements 202 and 204 is chosen to generate a reference voltage on the non-inverting input of the comparator 206 that corresponds to a specific detect signal intensity, for example −40 db. Therefore, by checking the voltage across capacitor 203 at specific times, the processor element 270 samples the strength of the antenna field.

Those skilled in the art will appreciate that the invention can be practiced in connection with other field intensity evaluation methods, specifically methods that use discreet analog to digital converters and methods that generate multi-bit representations of the signal strength of the received signal.

In accord with one embodiment of the invention, the transponder is operated in the following manner to determine lane position and linear distance from the stationery transceivers.

Referring again to FIG. 11, the transponder 228 of vehicle 212 is inactive as it approaches the antenna field 226 of transmitting unit 218. As the vehicle enters field 226, the early warning signal detection unit 278, places the processor 270 in active mode and the transponder begins processing the received signals.

Figure 16:
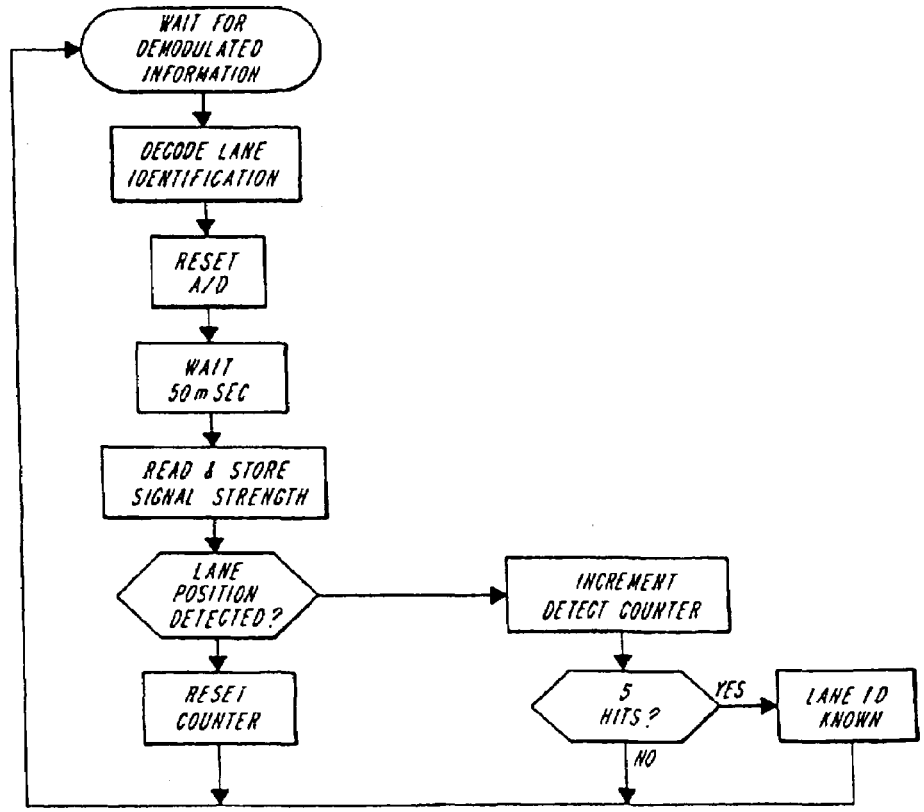
FIG. 16 is a flow diagram of the microprocessor code that determines the validity of a lane detection signal.

FIG. 16 is a flow diagram of the processor code for determining the vehicle lane position. As illustrated in FIG. 16, once the processor 270 is in active mode, the processor waits for the receiver unit 272 to send it the demodulated signal information. The processor 270 decodes the signal identification information and determines the identity of the lane that transmitted the received signal. The processor then resets the signal strength evaluation unit 276, so that this circuit is initialized to zero. The processor then waits a period of time for the signal strength evaluation unit to determine the strength of the signal. In the example given the processor element 270 waits 50 milliseconds, allowing the capacitor 203 to charge. At the end of 50 milliseconds the processor reads and stores the signal strength from this circuit.

Processor 270 then compares the measured signal strength to the known field pattern of the transmitting unit. If the signal strength indicates the vehicle is within the identified lane then the lane position counter associated with that lane identity is incremented. The processor then determines from a preset counter whether enough lane detections have been recorded to indicate a probability of the lane identification. In one example, five consecutive detections of a signal transmitted from the same lane, with a signal strength indicating the vehicle is in that lane, is sufficient to identify the lane position of the vehicle. Once the lane identity has been checked the signal strength, the processor returns to a wait condition.

In a further embodiment of the invention, the determined lane identification information is stored by the processor 270 in a register of memory 288. The lane identification information along with preassigned vehicle identity information, is then encoded into all signals transmitted from transponder 228 to the stationary transceiver units 218–222. In one example, transmitting units 218–222 are positioned above the lanes of an automated toll collection plaza or gentry. Transceiver units 218–222 control signals to vehicles approaching the tolls that require the vehicles to transmit information signals back to the transceiver unit above that vehicle's lane. In an apparatus constructed in accordance with the present invention, processor 270 retrieves the lane identity from the memory 288 and transmits the lane identity, along with other information, to the transceiver units 218–222. In this way, transceiver units 218–222 overcome the problem of multipathing by correlating each received signal to the correct vehicle.

In another aspect of the invention, a method for determining the position of a vehicle traveling on a multi-lane roadway is determined by the following steps. In the first step a transceiver unit is positioned above one lane of a multi-lane roadway and transmits through a highly directional antenna a signal encoded with lane identification information.

In a second step, a mobile transponder unit receives transmitted signals and processes these signals to determine lane information identification and the strength of the signal information. In a third step the lane identification information and signal strength information is processed to determine the vehicle lane position and distance from the stationary transceiver unit.

A further method comprises storing the lane identification information, so that it can be encoded in al transmissions from the mobile transponder to the transceiver units, in this way allowing the transceiver units to establish the lane position of the transmitting vehicle.

It will be understood that changes may be made in the above construction and in the foregoing sequences of operation without departing from the scope of the invention. In a further embodiment of the present invention, alternative algorithms are used to determine the position of the vehicle from the relative signal strength associated with each lane identity signal. For example, the relative signal strength of each lane identity signal is determined and compared to known field patterns for multi-lane roadways, and the probable adjacent lanes are determined. In this way, a relative determination of the mobile object's position is made from measurements of the field strength generated by each stationery transceiver unit.

In other constructions of the present invention, the illustrated radio frequency transmitters may be replaced by infrared transmitters or emitters operating in other regions of the electromagnetic spectrum. Moreover, the invention can be practiced in connection with railway or waterway vehicles, or for tracking packages.

Fixed Toll Road Operation

Figure 1:
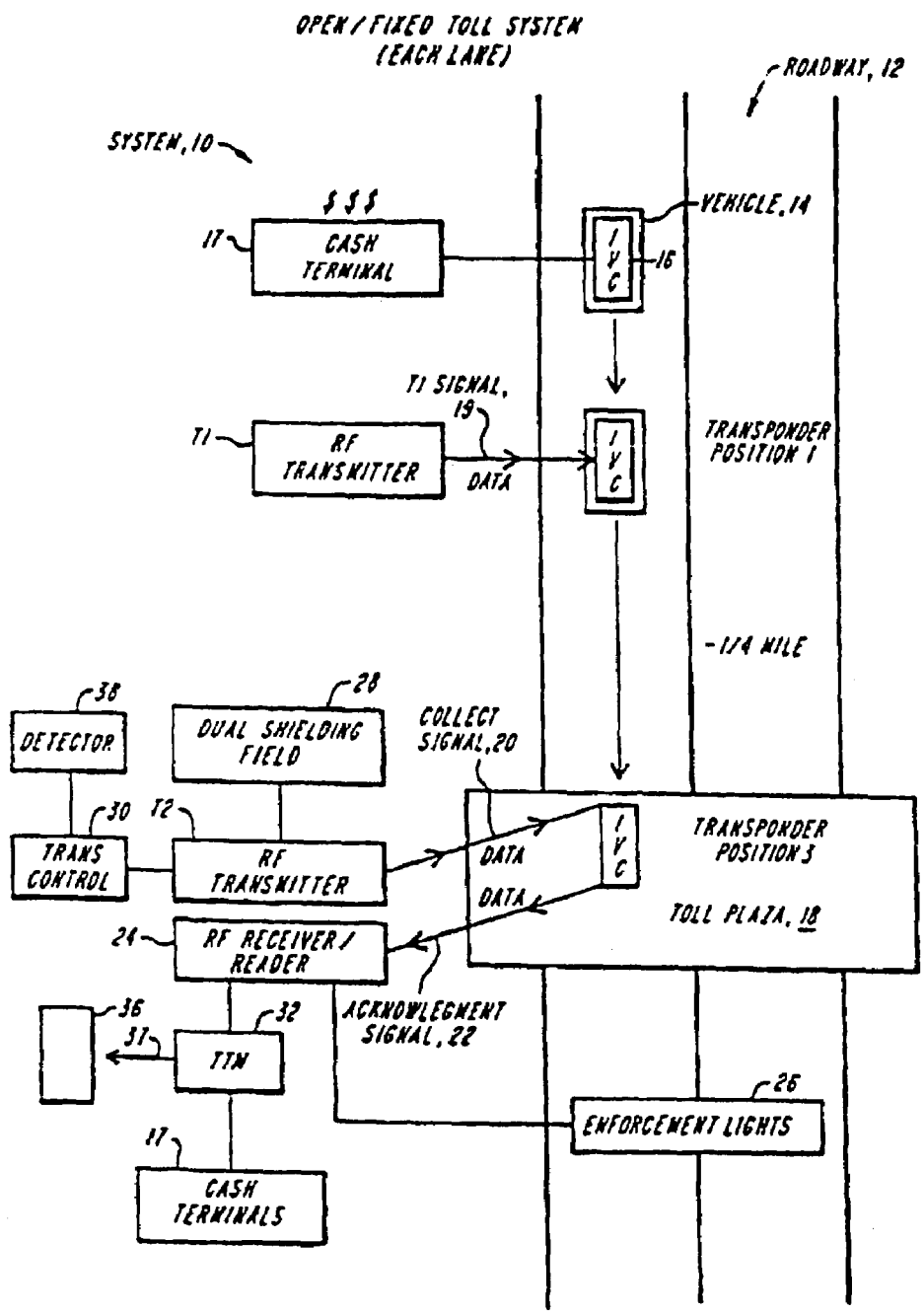
FIG. 1 is a schematic block diagram depicting an automatic toll collection system in accordance with the invention, adapted for use on fixed toll roads.

FIG. 1 depicts the overall structure and operation of an electronic toll collection system 10 constructed in accord with the invention, for use on fixed toll roads, or on bridges or tunnels. The illustrated embodiment enables automatic collection of toll charges from vehicles moving through a toll facility or plaza at speeds between zero and approximately sixty miles per hour. Vehicles need not halt or slow significantly for toll collection.

For purposes of simplicity, FIG. 1 shows only a single-lane road 12, on which the direction of travel for a given vehicle 14, referred to herein as the "downstream" direction, is indicated by arrows. Those skilled in the art will appreciate that the invention can be practiced in connection with multi-lane, divided roadways, or in railway networks or other transport systems.

The illustrated embodiment includes two primary components. The first is a communications system having two transmitter modules, referred to as T1 and T2. *These* transmitters will typically be owned by the toll authority and situated on toll authority *property*. *The* second component is an *in-vehicle* toll processor or *in-vehicle* component (IVC) 16 purchased or leased by vehicle *operators*. As described *below*, the IVC 16 contains a *transponder, microprocessor*, and *memory*, for *storing, manipulating*, and reporting on a quantity representative of money available to the vehicle for debiting in toll *transactions*. *The* IVC controls and processes *toll-related debit/credit transactions*, including extraction of toll *charges*, by communicating with T1 and T2.

As indicated in FIG. 1, the T1 transmitter is situated adjacent to the roadway 12, approximately one-quarter to one-half mile upstream from the toll plaza 18, such that vehicles moving at speeds between zero and approximately sixty miles per hour encounter the T1 signal well before encountering the toll plaza. The T1 module radiates an electromagnetic "toll-facility-identifier" signal that identifies the upcoming toll plaza. In the illustrated embodiment, the signal generated by T1 is a radio frequency (RF) signal.

The second transmitter module, T2, is situated at the toll plaza. The T2 module is a transmitter/sensor device that initiates the toll transaction by transmitting an encoded COLLECT signal 20, as described below.

In the embodiment depicted in FIG. 1, toll transactions occur in the following manner: At some time prior to the vehicle's arrival at the toll collection plaza, a toll authority agent at a toll credit facility 17 loads the IVC with a value representative of an initial toll-money-available quantity purchased by the vehicle operator. The IVC is also loaded with a code representative of the class of vehicle in which the IVC is installed. (This aspect of the invention is further described hereinafter.) The vehicle operator places the IVC in the vehicle and proceeds along the roadway. Approximately one-quarter mile to one-half mile from the toll plaza, the vehicle and IVC pass through a radio field 19 generated by transmitter T1. The T1 radio signal 19 contains a toll code identifying the upcoming toll collection facility. In one embodiment of the invention, the toll code also includes the toll schedule for the roadway, specifying the toll due for various classes of vehicles. For IVC units used only on fixed toll roadways, the schedule can be stored in the IVC.

Based on the information provided to the IVC by the T1 transmitter, the IVC calculates the appropriate toll due for the class of vehicle in which the IVC is installed. The IVC reads this information and interrogates its memory, to test whether a sufficient toll-money-available balance exists in the account corresponding to the toll authority for the roadway. If the toll-money-available quantity in the appropriate account exceeds the cost of the upcoming toll, the IVC generates a perceptible "PROCEED" message on an associated visual display element, to indicate to the vehicle operator that he or she may proceed through the automated toll facility.

If the cost of the upcoming toll exceeds the toll-money-available quantity for the relevant account, the IVC generates an appropriate alarm message, which can include, for example, an audible alarm and a visual display such as "INSUFFICIENT-MERGE LEFT." The vehicle operator is thereby advised to proceed to a standard toll booth.

Assuming a sufficient toll-money-available balance is indicated in the appropriate tollway authority account, a confirmatory user-perceptible signal is generated and the vehicle and IVC proceed to an electronic toll collection lane.

Referring again to FIG. 1, as the vehicle passes through the toll collection facility at a speed of approximately 0–60 miles per hour, the (T2) transmitter transmits a COLLECT signal 20 that instructs the IVC to debit the calculated toll amount from the toll-money-available quantity stored in its memory. In response, the IVC debits the calculated amount and transmits an acknowledgment signal 22 to the T2 indicating that the IVC has executed an appropriate debit transaction. As further described below, a reader unit 24 at the toll collection facility receives the acknowledgment signal and energizes a green light in an enforcement light array 26.

When the toll transaction is completed, the toll-money-available quantity stored in IVC memory is reduced by an amount corresponding to the toll, and the toll-money-available balance remaining in the account is displayed.

The IVC can store different toll-money-available signals corresponding to a plurality of toll authority accounts, in a manner described in greater detail hereinafter. A single IVC is thus operative for toll collection by multiple toll authorities. This feature of the invention is especially advantageous in geographical regions having roads, bridges and tunnels governed by several toll authorities.

While FIG. 1 depicts only one T2 module; governing a single lane, the invention can also be practiced in connection with multiple automated lanes, each governed by a respective one of a plurality of T2 transmitters. In order to reduce the possibility of RF crosswalk between multiple lanes, and to increase longitudinal discrimination between individual vehicles in a single lane, an RF shielding module 28 is provided. The operation and structure of the shielding field module is discussed below.

The illustrated system includes a transmitter control element 30, for directing the T2 transmitter to emit the COLLECT signal when the proximity of a vehicle is detected by a vehicle detector 38, a reader unit 24 for receiving the IVC acknowledgment signals, enforcement lights 26 for indicating vehicle class and identifying any vehicle that proceeds without generating a proper acknowledgment signal, a Toll Transaction Management (TTM) system 32 for recording toll transactions for the toll authority, and cash terminals 17 coupled to the TTM for enabling vehicle operators to purchase prepaid toll-money-available quantities. The structure and function of these elements are described in greater detail hereinafter.

FIG. 1 thus depicts an embodiment of the invention adapted for employment on fixed toll roadways. The invention can also be practiced on progressive toll roadways, in the embodiment depicted in FIG. 2.

Progressive Toll Road Operation

Figure 2:
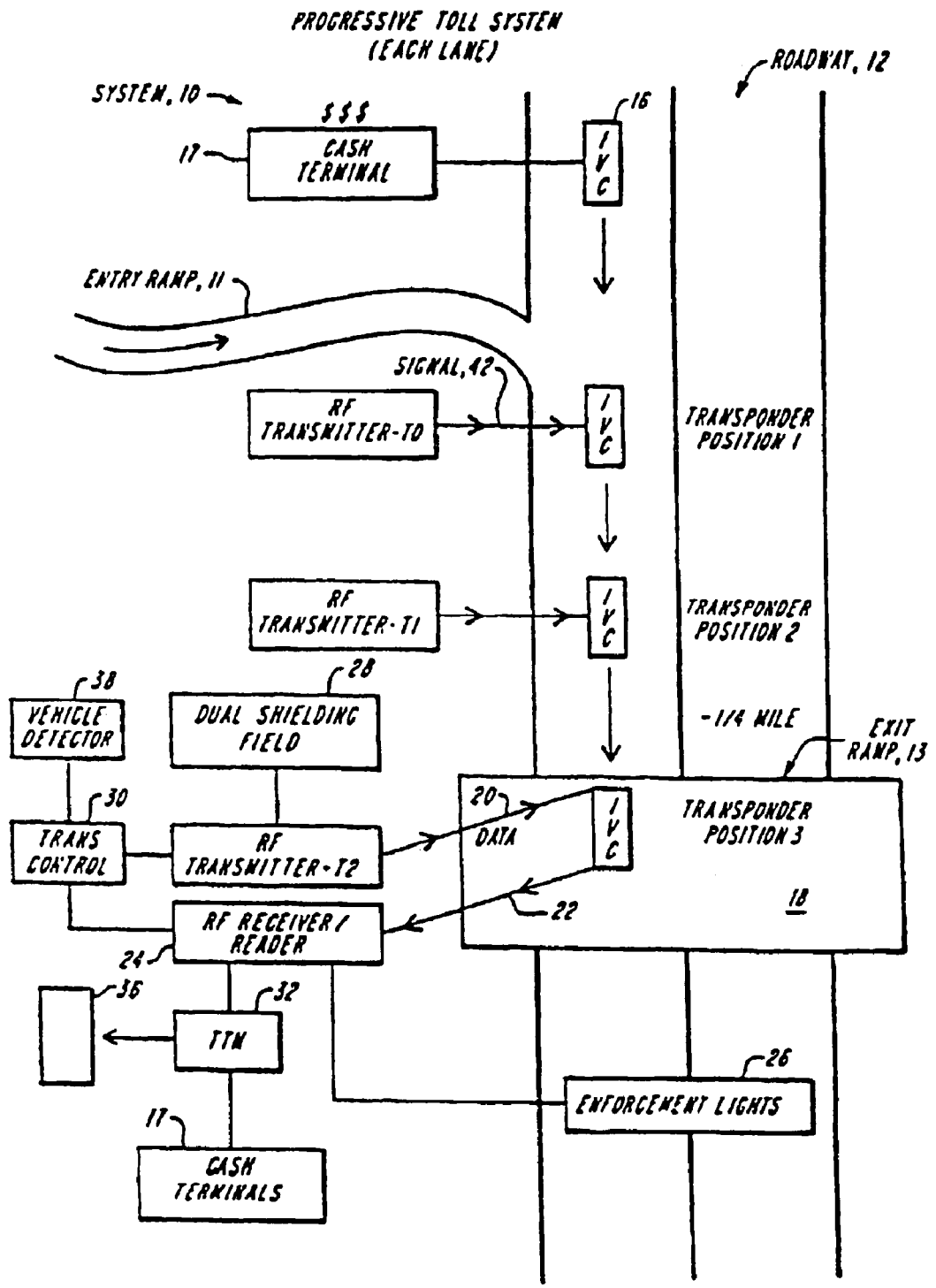
FIG. 2 is a schematic block diagram of another embodiment of the invention, adapted for use on progressive toll roads.

The system 10 illustrated in FIG. 2 is adapted for use on progressive tollways such as turnpikes, where toll values are calculated on the basis of known entry and exit points. On such roads, vehicles enter and exit the roadway via selected on-ramps and exit ramps, selecting a given exit and passing others. Typically, a separate toll facility is located at each exit ramp.

The progressive toll embodiment of the invention utilizes the IVC, T1, and T2 transmitters discussed above in connection with the fixed toll system. Additionally, as indicated in FIG. 2, another transmitter, referred to herein as a T0 transmitter, is located adjacent to each on-ramp 11 to the progressive toll road 12. Each T0 transmitter emits an entry-point-identifier signal 42 uniquely identifying the on-ramp to which the T0 corresponds. This signal is used to advise the IVC of the vehicle's entry point onto the progressive toll highway.

As the vehicle enters the tollway, the vehicle and IVC pass through the (T0) radio field that contains the encoded entry-point-identifier signal 42 specifying the entry ramp location or entry ramp number to the IVC. The IVC stores this information in its memory element.

Approximately one-quarter to one-half mile from each exit ramp plaza, the vehicle and IVC approach the T1 transmitter and receive the T1 encoded toll-facility-identifier signal identifying the upcoming exit ramp toll collection facility. The T1 signal also specifies the toll schedule for the roadway. This toll schedule includes distance/cost and vehicle class/cost data.

In response to the T1 signal data, and based on the T0 entry-point data stored in the IVC, the IVC calculates the appropriate toll due for the vehicle in which the IVC is installed.

The IVC reads this toll data and interrogates its memory to test whether a sufficient toll-money-available balance exists in the account corresponding to the toll authority for the roadway.

If the cost of the upcoming toll exceeds the toll-money-available quantity for the relevant account, the IVC generates user-perceptible alarm messages, which can include, for example, an audible alarm and a visual display such as "INSUFFICIENT FUNDS—MERGE LEFT." The vehicle operator is thereby advised to utilize a standard toll booth if the operator elects to exit the tollway at the upcoming exit ramp.

If the toll-money-available quantity in the appropriate account equals or exceeds the cost of the upcoming toll, the IVC generates a perceptible "PROCEED" message on its display element, to indicate to the vehicle operator that he or she may proceed through the automated toll facility if the operator elects to exit the tollway at the upcoming exit ramp.

Operation at the toll facility then proceeds in a manner similar to that described above in connection with the fixed toll embodiment of the invention.

If the operator of the vehicle elects not to exit the tollway at the upcoming exit ramp, and instead chooses to pass the current exit and proceed to a subsequent exit, the vehicle and IVC will encounter at the next exit ramp a subsequent T1 transmitter, corresponding to, and spaced apart from, the subsequent exit ramp toll collection facility. In response to receiving this new T1 signal, the IVC stores the new T1 data in memory, overwriting the old T1 data. The T0 entry-point information is retained, however, and the IVC executes a new toll calculation and toll-money-available test, based on the T0 data and new T1 information. This cycle is repeated for each automated exit facility that the vehicle operator elects to pass. The T0 entry-point information is erased from memory after receipt of a T2 TOLL-COLLECT signal at a toll collection facility, or upon receipt of new T0 data, which occurs when the vehicle re-enters a progressive toll road.

In the illustrated embodiments, the T1 transmitter is located approximately one-quarter to one mile from the T2 transmitter to avoid improper detection of T1 signals by IVC units approaching the toll facility from the opposite direction. Additionally, to assure that a T1 does not improperly reset an IVC approaching from the opposite direction before the IVC passes through its respective T2, the T1 transmitter can be angled towards oncoming traffic and away from the opposite direction of traffic.

The IVC

Figure 3:
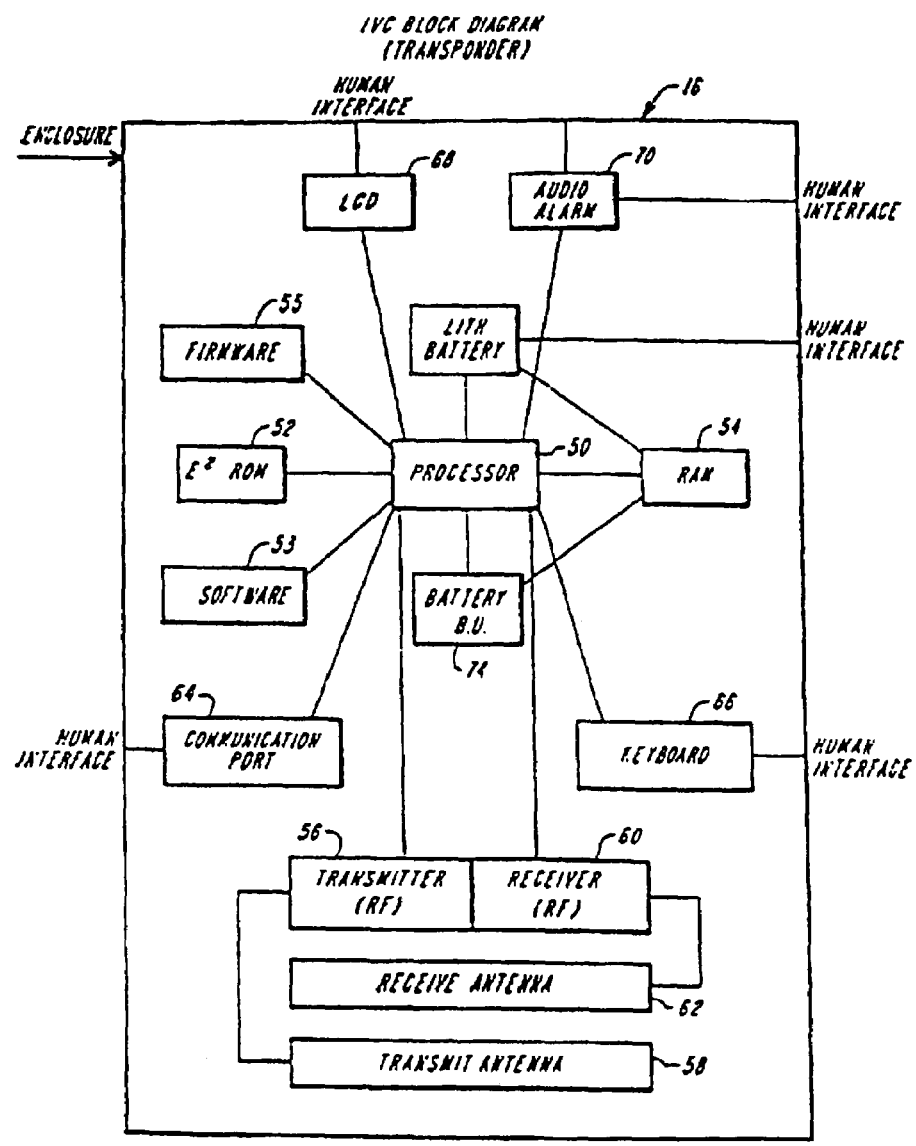
FIG. 3 is a schematic block diagram depicting detail of an in-vehicle component (IVC) utilized in the embodiments of FIGS. 1 and 2.

FIG. 3 depicts detail of the IVC 16. The IVC includes a processing element 50, an associated EPROM 52 for storing control software 53, a CMOS RAM element 54 for storing toll-money-available quantities and other data, control firmware 55, an RF transmitter 56 and associated antenna module 58, an RF receiver 60 and associated antenna module 62, user interface elements 66, 68, 70, a bi-directional communications port 64, and power supply elements.

The processing element 50 can be an 8086 or other microprocessor capable of executing the calculations necessary to determine toll amounts, based on a toll schedule received from T1 transmitters. The microprocessor also controls decoding and interpretation of encoded signals, in a manner described in greater detail hereinafter. The RAM element 54 preferably provides sufficient non-volatile memory to store toll data for a large number of toll authority accounts.

The IVC antennas 58, 62 can be incorporated into the IVC, or a receptacle can be provided to attach to a conventional window-mounted antenna, similar to those employed in connection with cellular telephone devices.

The user interface elements preferably include user-operable keys 66, LCD or LED display units 68, and an audio alarm module 70. The display and audio alarm elements provide visual or audible alarm signals when necessary, while the keys and display elements enable the vehicle operator to obtain information relating to toll-money-available quantities for each toll authority account stored in the IVC RAM. The display and user interface keys, in combination with conventional EPROM-stored software routines for controlling the microprocessor, enable the user to view the balances of each account stored in the IVC RAM. In one embodiment, the user interface includes an alphanumeric display having two lines of 10 characters each.

The bi-directional communications port 64 enables other microprocessors, including toll authority data processors, to write data into, and read data from, the IVC RAM. These read/write functions, which include purchase of gross toll quantities, diagnostic operations, and report generation, are discussed in greater detail hereinafter.

The power supply elements preferably include a compact, user-replaceable long-life battery 74, such as a lithium power cell. These elements can also include an on/off switch incorporating a battery check position.

The IVC components depicted in FIG. 3 are conventional in design and construction, and the IVC can be constructed in accord with known transponder and microprocessor control principles. The illustrated IVC transponder/processor can be housed in a compact, portable enclosure adapted for removable attachment to a dashboard surface or other convenient location within the vehicle.

The combination of components depicted in FIG. 3 enables the IVC to process fixed toll and progressive toll transactions. Additionally, the IVC can store and process different toll values for various toll authorities, toll facilities, and toll booths, so that a single IVC can accommodate multiple toll authorities and the expanded progressive toll tables required for multiple vehicle classes.

In particular, the IVC receives, decodes, and stores the T1 transmitter signal, interprets the stored signal, calculates the required toll amount based upon the stored signal, store the calculated toll amount, and debits the calculated amount at the toll facility in response to a COLLECT signal from the T2 transmitter. The IVC debits the calculated toll quantity from the appropriate account and transmits an acknowledgment signal that includes a vehicle-class message and confirmation of the debit operation.

As discussed in further detail below, the acknowledgment signal takes the form of an encoded logical response to the COLLECT signal from the T2 transmitter. The acknowledgment is dependent upon the content of the COLLECT message.

Following transmission of the acknowledgment, the IVC remains inactive until it passes through another T1 field. The IVC thus consumes power intermittently, and only when required for toll data processing. This feature reduces average power demands, and significantly extends battery life.

IVC Data Fields

In one practice of the invention, toll account information stored in the IVC includes individual toll road files having data fields with the following information:

| Field | Size |
| --- | --- |
| Start File | 2 bits |
| Toll Facility Name | 10 bits |
| Previous Balance | 6 bits |
| Amount Debited | 6 bits |
| Amount Credited | 6 bits |
| Current Balance | 6 bits |
| End File | 2 bits |

Those skilled in the art will appreciate that the invention can be practiced in connection with other data field parameters.

Each data file can be manipulated and edited as required for individual transactions between the IVC and the toll collecting T2 module, or between the IVC and the toll authority data processing system, as described in greater detail hereinafter.

IVC Operational States

In accord with one embodiment of the invention, the IVC unit can utilize the following operational states:

| State Number | Description |
|---|---|
| 0.0 | IVC off. |
| 1.0 | IVC switched on. |
| 1.1 | Upon switching on, lack of response signifies that the system is inoperable. |
| 1.2 | Upon switching on, system comes up, executes battery check, displays "OK" message, sounds beep. |
| 1.2.1 | Upon switching on, system comes up, executes battery check, detects low battery condition, displays "LOW BATTERY" message, sounds beep. |
| 1.2.2 | IVC enters hibernation—a state in which little or no power is consumed, and the IVC waits to sense a signal. |
| 1.2.3 | IVC detects a transmission, exits hibernation and prepares to read encoded message. |
| 1.2.3.1 | Attempts to read message, fails three times, displays "error" and "proceed", sounds beep. |
| 1.2.3.2 | Reads message correctly, verifies correct read. |
| 1.2.3.2.1 | Checks whether message is T0, T1, T2. |
| 1.2.3.2.1.1 | Determines that message is T0. |
| 1.2.3.2.1.1.1 | Sounds beep, deletes from memory all current travel data"—i.e., current memory for current trip. |
| 1.2.3.2.1.1.2 | Saves to "travel data" record, enters hibernation |
| 1.2.3.2.1.2 | Determines that message is a T1 record, will not read another T1 record for 2 minutes. |
| 1.2.3.2.1.2.1 | Determine whether T1 message is fixed or progressive. |
| 1.2.3.2.1.2.1.1 | Determines that T1 record is progressive |
| 1.2.3.2.1.2.1.1.1 | Looks for T0 in "travel data" memory, not found. |
| 1.2.3.2.1.2.1.1.1.2 | Sounds beep, displays "error" and "proceed". |
| 1.2.3.2.1.2.1.1.1.3 | Enters hibernation. |
| 1.2.3.2.1.2.1.1.2 | Looks for T0 in "travel data", finds T0 record |
| 1.2.3.2.1.2.1.1.2.1 | Sounds beep, displays "OK", calculates toll due at next T2 based on comparison between T0 record and current record, deletes previous T1 record if any in "travel data". |
| 1.2.3.2.1.2.1.1.2.2 | Enters hibernation. |
| 1.2.3.2.1.2.1.2 | Determines T1 record is of fixed toll type. |
| 1.2.3.2.1.2.1.2.1 | Deletes previous T1 record (if any in "travel data"). |
| 1.2.3.2.1.2.1.2.2 | Sounds beep, displays "OK", calculates toll. |
| 1.2.3.2.1.2.1.2.3 | Goes into hibernation. |
| 1.2.3.2.1.3 | Determines the message is a T2 record. |
| 1.2.3.2.1.3.1 | Returns acknowledgment encoded with vehicle type, deletes toll amount from specified account. |
| 1.2.3.2.1.3.2 | Sounds beep, displays "OK", "Thank You". |
| 1.2.3.2.1.3.3 | Clears all "travel data". |
| 1.2.3.2.1.3.4 | Enters hibernation |

If an IVC having no "Travel Data" in memory receives a T2, it reads the default toll from T2 record and deletes the default amount from the appropriate account.

IVC Toll Calculation Logic

Fixed Tolls: The IVC passes through a fixed-toll T1 field and receives an encoded T1 record indicating a fixed toll. The IVC then calculates the toll due at the next T2 site, based on the fixed rate found in the toll schedule field. If the IVC passes through another T1 prior to encountering a T2 field, the IVC deletes the old T1 record and replaces it with the new T1 record.

Progressive Tolls: The IVC passes through a T1 field and the encoded T0 record is stored future processing. This record includes the following:

| | |
|---|---|
| 1. Start message | 2 bits |
| 2. Toll facility identifier | 6 bits |
| 3. Direction identifier | 2 bits |
| 4. T0 identifier | 2 bits |
| 5. End message | 2 bits |

Upon receiving a T0 message the IVC deletes all "Travel Data" in memory.

As the IVC passes through a T1 field, it receives an encoded record indicating a progressive toll, as follows:

| | |
|---|---|
| 1. Start message | 2 bits |
| 2. Toll facility identifier | 6 bits |
| 3. Direction identifier | 2 bits |
| 4. T1 identifier | 2 bits |
| 5. Toll type (progressive or fixed) | 2 bits |
| 6. Toll schedule | 256 bits |
| 7. End message | 2 bits |

Having received the T0 and T1 records, the IVC calculates the toll due at the next T2 it encounters. If the IVC passes through another T1 field before it encounters a T2, the IVC deletes the previous T1 record, replaces it with the new T1 record, and recalculates the toll due.

Upon passing through to a T2 the IVC debits the appropriate toll from the specified IVC toll authority account.

The entire T2 record includes the following:

| | |
|---|---|
| 1. Start message | 2 bits |
| 2. T2 identifier (simply states that the transmitter is a T2) | 2 bits |
| 3. Toll authority/booth identifier | 6 bits |
| 4. Direction identifier | 2 bits |
| 5. Default toll amount | 8 bits |
| 6. End message | 2 bits |

These T0 and T1 records contain all data required for calculating a progressive toll. The direction identifier can be use in error detecting calculations.

The 256 bit toll schedule field in the progressive-toll T1 record is a matrix of toll values based on entry points (A–C in this example) and exit points (A–C) specified in the T0 and T1 records, respectively:

| | A | B | C |
|---|---|---|---|
| A | 0 | $ | $ |
| B | $ | 0 | $ |
| C | $ | $ | 0 |

T0, T1 Transmitters

Figure 4:
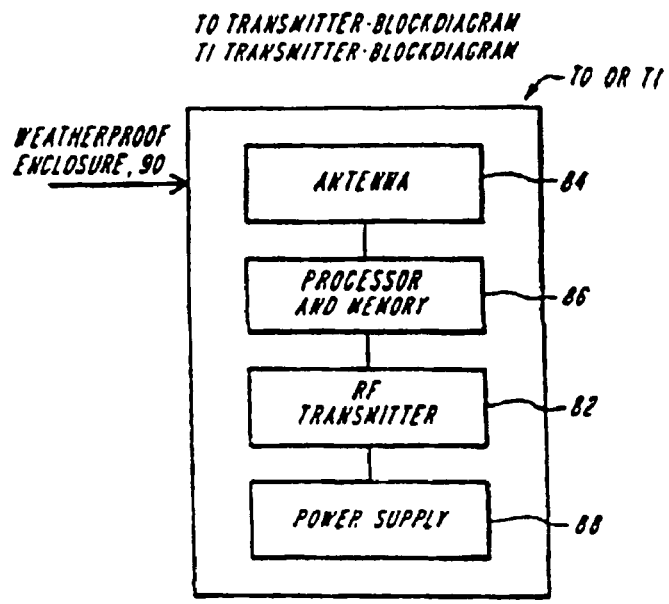
FIG. 4 is a block diagram depicting detail of T0 and T1 transmitters constructed in accord with the invention.

FIG. 4 depicts the structure of entry ramp transmitters T0 and toll-facility-identifier transmitters T1 constructed in accordance with the invention. Those skilled in the art will appreciate that while the illustrated T0 and T1 transmitters utilize radio frequency signal generating elements, the invention can also be practiced in connection with transponder components utilizing infra-red (IR) or other radiant electromagnetic energy wavelengths.

As discussed above, the T0 transmitters and T1 transmitters repeatedly emit an encoded signal that provides the IVC transponder elements with data required for toll calculation and collection.

The T0 toll-facility-identifier signal field is encoded with the following record:
1. Start message flag.
2. Toll identifier (identifies toll facility)
3. Direction identifier
4. T0 identifier (not a number, simply identifies signal source as a T0)
5. End message flag.

The T1 message is encoded with the following record:
1. Start message
2. Toll identifier (identifies toll facility)
3. Direction (A or B)
4. Toll schedule
5. T1 identifier (not a number, simply identifies signal source as a T1)
6. Toll type (progressive or fixed)
7. End message The toll schedule identifies tolls and their breakdown by vehicle type. The T1 signal is incrementally receivable, in that the IVC checks for the required data among the received messages and stores only the message it requires.

The START and END message bits are significant in assuring that individual IVC units read only complete messages, and do not attempt to read a message already in progress.

Each of the illustrated transmitter units T0, T1 includes a conventional RF transmitter 82 and antenna element 84, microprocessor and associated erasable programmable read-only memory (EPROM) 86, and power supply elements 88. The EPROM stores software for control and operation of the transmitters. These components are conventional in design and materials, and the transmitters can be constructed in accordance with known engineering practice. The complete T0 and T1 assemblies are preferably enclosed in a rugged weatherproof housing 90, to withstand the ranges of temperature, humidity, and ultraviolet radiation typical of the roadway environment. The T1 transmitter can be activated by an infra-red or optical vehicle detector, so that the T1 transmitter emits signals only when a vehicle is in proximity to the transmitter.

T2 Transmitter

Figure 5:
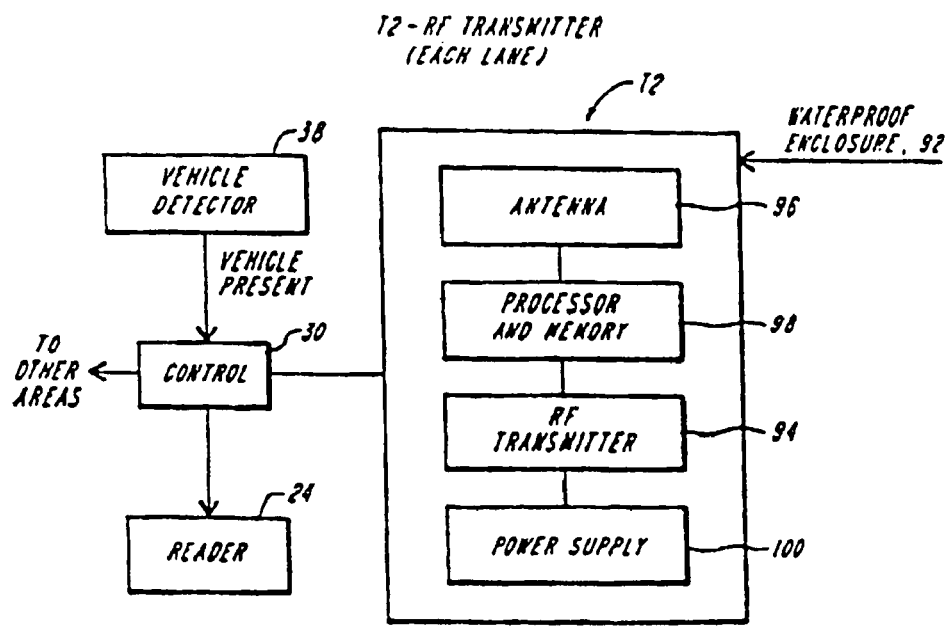
FIG. 5 is a block diagram depicting a T2 transmitter subsystem constructed in accord with the invention.

FIG. 5 depicts a toll-collect transmitter T2 in accord with the invention, for transmitting a TOLL-COLLECT signal instructing the IVC to debit the calculated toll amount. In one embodiment of the invention, the TOLL-COLLECT signal is a digital signal containing four bytes of data.

The T2 transmitter is preferably enclosed in weatherproof housing 92, and includes a conventional RF transmitter module 94 and associated antenna elements 96, a microprocessor, an EPROM for storing control software 98, and power supply elements 100. While the illustrated T2 transmitter includes radio frequency signal generating elements, the invention can also be practiced in connection with transponder components utilizing infra-red (IR) or other radiant electromagnetic energy wavelengths.

The T2 signal is encoded with the following information:
1. Start message flag.
2. T2 identifier (not a number, simply states it is a T2).
3. Toll identifier (includes toll authority and toll booth)
4. Direction identifier
5. Default toll amount—the amount debited if the T0 entry-point-identifier is lost or otherwise not present.
6. End message flag.

Toll Facility Hardware

In the embodiment depicted in FIGS. 1 and 5, the T2 transmitter is electrically connected to a transmitter control unit (TCU) 30 and a vehicle detector 38. The vehicle detector can be, for example, a photoelectric cell, located within ten to fifteen feet of the T2 transmitter, for optically sensing the presence of a vehicle and generating a VEHICLE PRESENT signal. When the VEHICLE PRESENT signal is relayed to the TCU, the TCU directs the T2 transmitter to transmit the COLLECT message. Thus, the T2 transmitter for a given lane emits a COLLECT signal only when a "target" vehicle is present in the lane, as indicated by the VEHICLE PRESENT signal.

The transmitter control unit is also interconnected with an acknowledgment signal reader unit 24. The reader unit 24, which utilizes conventional RF receiver elements, receives acknowledgment signals—and the vehicle-class identifiers contained therein—from each vehicle's IVC, to confirm that a toll debit transaction has been completed. The reader unit can be mounted on the leading edge of the toll facility canopy, angled downward toward oncoming traffic. Multiple reader units covering one direction of traffic at a single toll barrier can be connected to a reader control unit (RCU) that executes diagnostics, records activity in each lane, and forwards records of the activity to the TTM for further processing.

Figure 6:
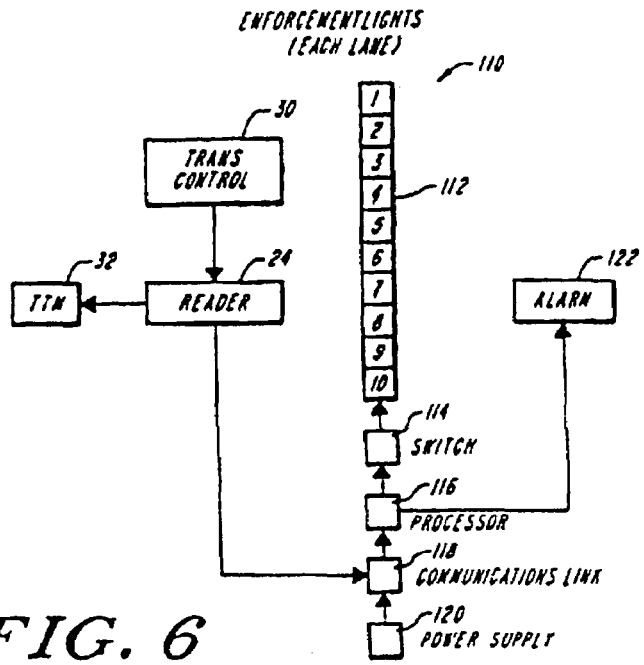
FIG. 6 depicts an enforcement subsystem utilized in the embodiments of FIGS. 1 and 2.

Each time the reader unit receives an acknowledgment signal, the reader unit transmits the vehicle identifier to the enforcement subsystem depicted in FIG. 6.

The enforcement subsystem 100 is provided to reduce the possibility of toll evasion. More particularly, in automated toll collection systems utilizing a conventional enabling device such as a magnetic card, tolls can be evaded by utilizing an enabling device designated for a low-toll vehicle class, such as an automobile, in a truck or other high-toll vehicle. The enforcement subsystem 100 addresses this problem. The subsystem shown in FIG. 6 governs one automated lane. It includes a vertical array of ten indicator lights 112 housed within a weatherproof, substantially cylindrical enclosure; a switch unit 114, a processor 116, a communications link 118, a power supply 120, and an alarm 122. Each indicator light in the light array represents a different class of vehicle—bus, car, truck, or other. The microprocessor 116 controls the switch 114 to energize a selected indicator light, in response to signals from the reader unit 24 for the lane. Signals generated by reader unit 24 are relayed to the processor 116 via communications link 118.

Each time the reader unit 24 receives an acknowledgment signal and vehicle-class identifier from an IVC in the lane, the reader transmits the vehicle-class identifier to the communications link, processor, switch, and light column, thereby causing a single selected indicator light to be energized. The selected light is representative of the vehicle class specified by the IVC in the vehicle currently passing through the corresponding lane of the toll facility. Enforcement personnel can then monitor the light column for each automated lane to confirm proper correspondence between visually observed vehicle class and vehicle class indicated by each IVC. Lack of proper correspondence indicates that the IVC in the current vehicle is incorrectly initialized for the class of vehicle in which the IVC is installed.

Moreover, if the vehicle detector for a given lane detects a vehicle, but the reader does not receive a proper acknowledgment signal within a predetermined interval of time, the enforcement processor activates the alarm module. The alarm module can include audible and visible alarm elements such as buzzers and strobe lamps.

RF Isolation

Figure 7:
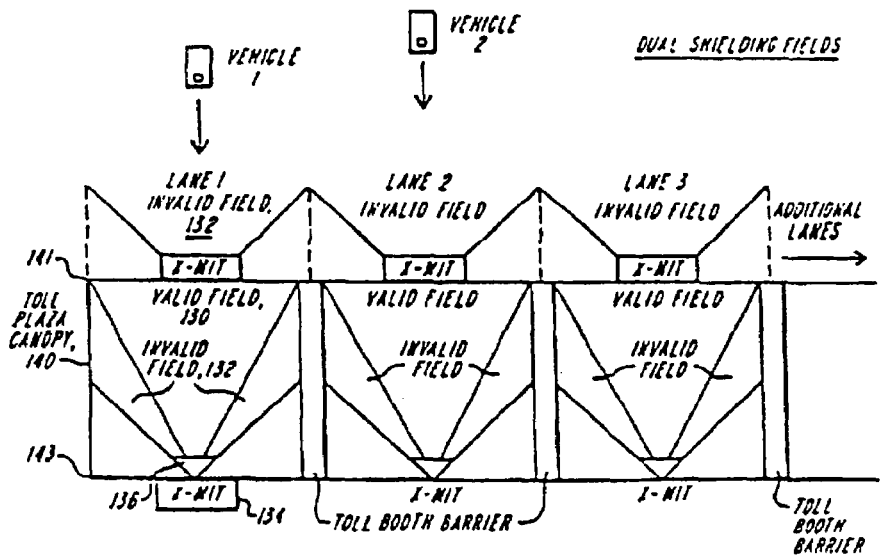
FIG. 7 depicts RF shielding fields generated in accord with the invention.

When the invention is practiced in a multiple-lane embodiment, the possibility exists that an IVC or reader unit operating in one lane will inadvertently detect signals generated by transmitters operating in adjacent lanes. The resulting confusion could frustrate system users or permit toll evaders to exploit the automated system. Consider, for example, first and second vehicles and respective IVC units approaching a multi-lane automated toll facility in adjacent first and second lanes, as depicted in FIG. 7. For purposes of this example, the second vehicle is behind the first. When the first vehicle enters the toll collection zone in the first lane, the T2 transmitter for the first lane transmits a TOLL COLLECT signal. In the absence of appropriate isolation, the second IVC, in the second lane, may receive the COLLECT signal intended for the first vehicle, and transmit an acknowledgment before reaching the second lane toll collection zone. The second vehicle's IVC would subsequently fail to generate the appropriate acknowledgment signal when it reaches the second lane collection zone.

Conversely, without proper isolation, the acknowledgment generated by the first IVC in the first lane may enable a toll evader in the second lane to pass through the second lane toll collection zone without generating a proper acknowledgment, and without triggering an alarm.

Thus, certain measures must be employed to reduce the possibility of RF crosswalk between multiple lanes, and to increase longitudinal discrimination between individual vehicles in a single lane.

To permit the reader unit to discriminate between an acknowledgment from a target vehicle IVC and "false" acknowledgments from adjacent vehicles or other sources, the control unit (FIG. 5) prevents the reader unit from detecting acknowledgment signals until the vehicle detector generates a VEHICLE-PRESENT signal indicating physical proximity of a vehicle in the lane.

Additionally, each IVC is programmed to generate its acknowledgment signal within a predetermined number of milliseconds after the T2 transmitter emits the COLLECT signal, and the corresponding reader unit checks for the acknowledgment only during this time window. Enabling the reader unit only when a VEHICLE-PRESENT signal is generated, and using a limited time window for acknowledgment transmission and detection, provides a temporal distribution of acknowledgment signals, thereby reducing the probability that a reader unit for a first lane will detect an acknowledgment from an IVC in an adjacent second lane.

Isolation can also be provided by controlling the transmission time of TOLL-COLLECT signals transmitted from adjacent lanes such that transmission of TOLL-COLLECT signals and subsequent detection of acknowledgment signals occurs serially, in only one vehicle lane at a time.

Another approach involves enhancement of RF isolation by configuring the T2 module to generate dual RF fields, as depicted in FIG. 7. One field 130, directed at the intended incoming target vehicle, carries a valid encoded TOLL-COLLECT message. A second field 132, directed at vehicles behind and on either side of the target vehicle, effectively isolates nearby vehicles from the COLLECT message, so that only the target vehicle, which is in close proximity to the T2 transmitter and the reader unit, can receive the T2 TOLL-COLLECT message and generate an acknowledgment. The continuously repeating shielding field signal 132 is not encoded, but in one embodiment of the invention is used to initialize incoming IVC units by incorporating values instructing the IVC units to prepare to receive a valid, encoded COLLECT signal.

RF shielding elements in accord with the invention, including transmitters 134, antennas 136, and shielding fields 132, are depicted in FIG. 7. The illustrated embodiment utilizes multiple shielding field transmitters 134 having antennas 136 oriented at selected angles to generate overlapping radio fields. This configuration isolates, or shields, a selected "VALID" region in which a T2 TOLL-COLLECT signal or other "VALID" transmission can be received. The shielding transmitters 134 utilize at least two antennas 136. These emitters continuously transmit a time-invariant RF signal that is not encoded. The shielding signal is thus a NO-OP or NO-COLLECT signal that IVC units do not recognize as an instruction to execute a debit operation.

As indicated in FIG. 7, the shielding field RF transmitters 134 and associated antennas 136 are arranged to provide fields 132 having overlapping lobes. Within the shielding field overlap regions, the average amplitude of the shielding signal is higher than that of the T2 COLLECT signal, effectively "blanking out" the COLLECT signal. This configuration provides RF isolation between vehicles in adjacent lanes.

Operation of the shielding elements exploits the fact that the IVC will recognize a COLLECT message only in those regions where sufficient "VALID" signal amplitude is present—i.e., in the "VALID" regions where shielding field lobes do not overlap.

The shielding field antennas 136 can be mounted in selected locations on the toll facility canopy 140, and each antenna can be rotated to-selected angular orientations with respect to other antennas in the subsystem, to optimize RF isolation between vehicles and lanes. Preferably, a number of shielding field antennas 136 are located on the leading edge 141 of the toll facility canopy 140, oriented generally toward on-coming traffic, and angled approximately 45 degrees downward from the horizontal plane. Shielding signals of either a single frequency or multiple frequencies can be generated by one or more shielding field transmitters 134.

Isolation between multiple vehicles in a given lane, and isolation from T2 signals from adjacent lanes, is enhanced by utilizing directional antennas in the T2 transmitters, to focus the emitted T2 radio field downward onto oncoming vehicles.

In operation, when the IVC approaches the toll plaza, having already calculated the appropriate toll, the IVC encounters the shielding field, and responds by preparing to receive the encoded "valid" T2 field. The T2 "valid" transmitter, which can be mounted on the toll collection facility canopy approximately midway between the leading and trailing edges 141, 143 of the canopy 140, transmits its TOLL-COLLECT instruction when triggered by the vehicle detector. The IVC debits the toll amount and responds within a predetermined time interval by transmitting a message simply confirming the debit transaction and identifying the vehicle type. In one embodiment of the invention, this acknowledgment signal is a digital signal containing four bytes of digital data.

The RF shielding system can also be used in conjunction with T0 on-ramp transmitters, by transmitting a non-encoded second field that shields vehicles traveling on the progressive toll roadway from the T0 on-ramp signal.

The illustrated shielding field configuration can also be employed for position detection. In particular, when a signal having a selected frequency is transmitted at different amplitudes from each of the antennas, the relative position of a receiver with respect to the antennas can be determined on the basis of amplitude variations in the received signal as the receiver passes through the overlapping shielding fields. When signals of different frequencies or encoded variations of a single frequency are transmitted from each of the antennas, the relative position of a receiver with respect to the antennas can be determined from differences between received signals as the receiver passes through the overlapping shielding fields.

Toll Transaction Management

In order for an automated toll system to gain wide acceptance, it should provide information and records for accurate accounting of traffic activity and toll transactions at each toll booth and toll facility. The system should also expedite the toll purchase process.

Figure 8:
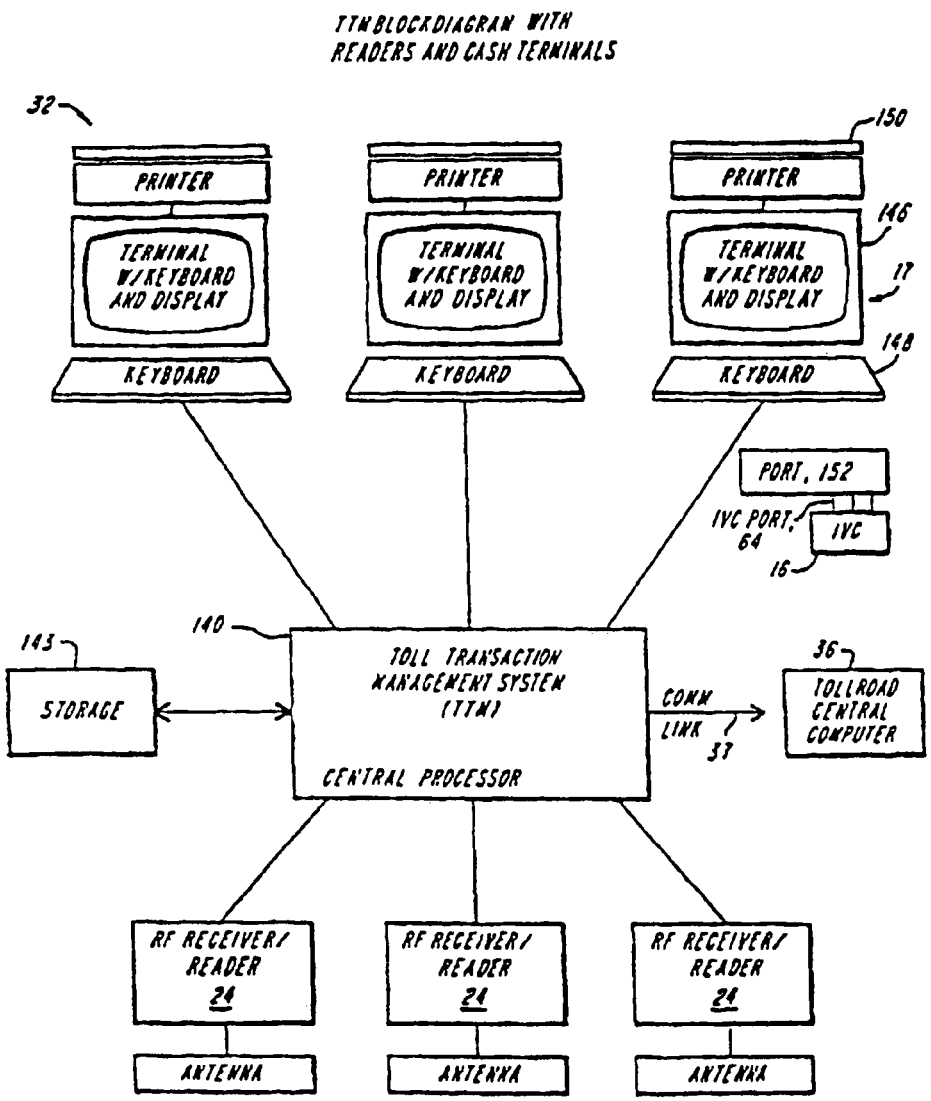
FIG. 8 is a block diagram of a Toll Transaction Management (TTM) systems utilized in the embodiments of FIGS. 1 and 2.

These advantages are provided in one practice of the invention by the Toll Transaction Management (TTM) subsystem 32 depicted in FIG. 8, which monitors toll collection, enables toll purchase and IVC loading, and generates reports on toll purchase, toll collection, and traffic activity.

The TTM subsystem 32 maintains records of all cash transactions—i.e., toll amount purchases—and automated toll debit transactions. These records are maintained and formatted for periodic down-loading to the toll authority central computer. The TTM can also execute diagnostic tests on each IVC as required, and verify the status of the toll accounts in each IVC, as described in greater detail hereinafter.

The TTM subsystem includes a central processor 140, cash terminals 17 in communication with the central processor 140, and a communications link 37 for bi-directional data communications with a toll authority central computer 136. The subsystem can also include a data memory and storage module 143 having conventional RAM, magnetic, optical or other digital data memory and storage elements.

The TTM central processor 140 can be a conventional microcomputer or minicomputer, depending upon the size and data-handling requirements of the automated toll system. The central processor is interconnected with the reader units 24 in each automated lane, to gather toll collection data including vehicle-class-identifiers, transaction time, and lane-by-lane traffic activity information. Where required, remote communication between the reader units and TTM central processor can be provided by modems or other data communications devices.

The cash terminals 17 include a conventional display 146, keyboard 148, and printer 150. The terminals also include an RS-232 or other conventional communications port 152 adapted for connection to a similar port 64 on each IVC unit (See FIG. 3). Using the communications port 152, the cash terminals 17 enable vehicle operators to credit their IVC accounts—i.e., load selected toll-money-available quantities—by prepaying selected toll amounts.

When a motorist wishes to prepay tolls and load the IVC, the motorist proceeds to a local toll facility and gives the IVC to a toll collection agent with cash or a credit card authorization equal to the toll amount the motorist wishes to prepay. The toll collection agent connects the IVC communications port 64 to the cash terminal communications port 152, and enters into the cash terminal the monetary amount to be stored in the IVC memory for a specified toll authority account.

The cash terminal 17 transmits a signal to the IVC 16, indicating a credit for the specified monetary amount to the selected account in the IVC. The cash terminal also prints a receipt verifying the credit to the account. This receipt can specify all toll transactions involving the IVC since the previous cash transaction. The cash terminal 17 then communicates with the Toll Transaction Management (TTM) central processor 140 to confirm the cash transaction. This information is retained in the memory 143 of the TTM for further processing, storage, and communications with the toll agency central computer.

In addition to toll purchases and other cash transactions, the cash terminal 17 can also interrogate individual IVC units 16 to produce printed diagnostic reports or travel data reports.

As indicated in FIG. 8, the TTM central processor 140 is connected to each reader unit 24 in the toll facility. When a reader unit 24 receives an acknowledgment and vehicle-class identifier from an IVC, the reader unit 24 relays the vehicle-class identifier to TTM central processor 140 for formatting, further processing, and storage. The formatted record generated by the TTM for each debit transaction is referred to as a Toll Transaction Record.

In addition to Toll Transaction Records, the TTM subsystem configuration depicted in FIG. 8 is capable of generating various records for use by each toll authority. While the number and type of such records will vary, depending upon toll authority requirements, the TTM subsystem can generate Cash Transaction Records, Traffic Records, and Cash Summary Records. The Cash Transaction Record is generated by the TTM, as described above, each time a motorist credits his or her IVC accounts by prepayment of a selected toll amount.

The TTM generates Traffic Records by summarizing relevant data from each incoming Toll Transaction Record. The Traffic Record is then relayed to the Toll Authority's central computer. The Cash Summary Record is generated by the TTM by processing all incoming Cash Transaction Records. The Cash Summary Record is also transmitted to the Toll Authority's central computer. Examples of data fields for each of these records is set forth below.

Because each of these records is intended for ultimate use by different toll authority computers, a standard data format should be utilized for communications with external toll authority processors. Current research indicates that most toll authority computers can read and write ASCII flat files. Thus, in one practice of the invention, the TTM generates files having an ASCII format, enabling standardized output to toll authority computers.

The TTM functions of creating and sorting records based on cash transactions, debit transactions, and traffic activity in each lane, can be provided by utilizing a commercially available database program such as Oracle or Dbase III.

Traffic and financial transaction records can be stored, tracked and displayed on the TTM cash terminal display units 146.

In addition, a plurality of TTM subsystems can be distributed along a progressive toll road, with conventional network communications between the TTM subsystems and a mainframe computer at the toll authority headquarters.

TTM Data Fields

Each of the TTM Records described above contains selected information relating to toll transactions. Data fields utilized in one practice of the invention are set forth below, by way of example. Those skilled in the art will recognize that the invention can be practiced with data fields other than those set forth below. In each case, data can be transferred to the TTM on a real-time basis as fixed format ASCII records. Each record is terminated by a carriage return/line feed sequence and commences with a "record type" indicator. Whenever a date is required, fields can be date and time stamped in a year-month-day-hour-minute-second format.

TOLL COLLECT DATA FIELDS

| FIELD | SIZE | DEFINITION |
| --- | --- | --- |
| record type | 2 | identifies record type |
| barrier/lane number | 8 | 4 digits identify barrier number |
| | | 4 digits identify lane number |
| vehicle type | 4 | identifies vehicle type |
| end message | hard rtrn | ends record |

TOLL PURCHASE/CASH TRANSACTION DATA FIELDS

| FIELD | SIZE | DEFINITION |
| --- | --- | --- |
| record type | 2 | identifies record type |
| barrier/lane number | 8 | 4 digits identify barrier number |
| | | 4 digits identify lane number |
| IVC serial num. | 8 | identifies IVC unit |
| amounted credited | 6 | amount purchased 9999.99 |
| current balance | 6 | current balance 9999.99 |
| end record | hard rtrn | ends record |

TRAFFIC RECORD DATA FIELD

| FIELD | SIZE | DEFINITION |
| --- | --- | --- |
| record type | 2 | identifies record type |
| from date/time stamp | 14 | record covers from–to |
| current date/time stamp | 14 | record covers from–to time |
| barrier/lane number | 8 | 4 digits identify barrier number |
| | | 4 digits identify vehicle type |
| vehicle type | 4 | 4 digits identify vehicle type |
| vehicles through | 6 | 6 digits identify number |
| " | | of vehicles through lane |
| " | | (8 vehicle types, repeats |
| " | | based on number of lanes |
| " | | in system) |
| end record | hard rtrn | ends record |

CASH SUMMARY DATA FIELD

| FIELD | SIZE | DEFINITION |
| --- | --- | --- |
| record type | 2 | identifies record type |
| from date/time stamp | 14 | record covers from–to |
| current date/time stamp | 14 | record covers from–to |
| Terminal num. | 4 | identifies cash terminal |
| total cash in | 6 | total cash in |
| | | (repeats last two fields for |
| | | every cash terminal in system) |
| end record | hard rtrn | ends record |

Signal Encoding

Figure 9:
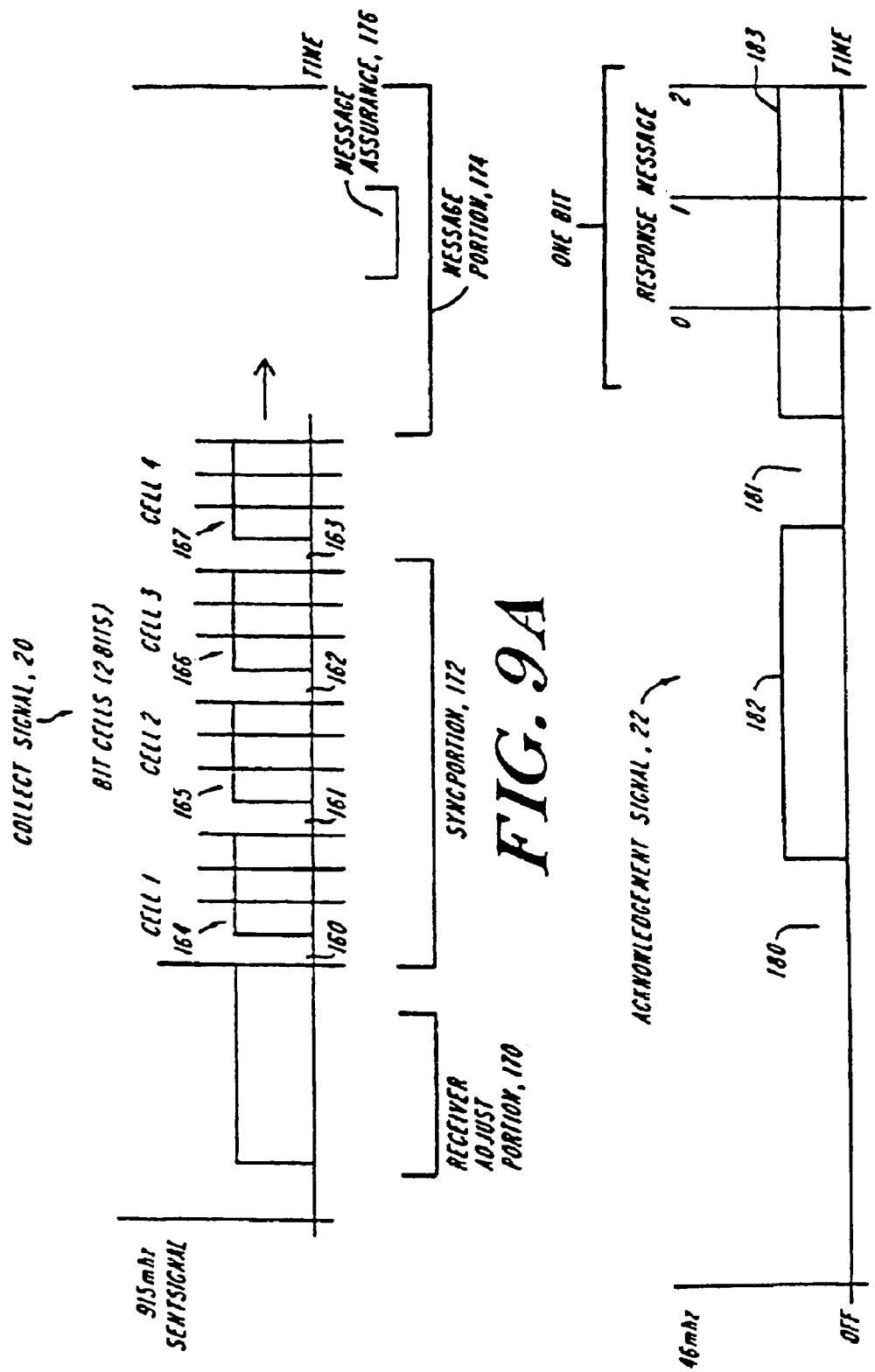
FIGS. 9A and 9B depict a simplified form of the COLLECT signal generated by the T2 transmitter, and a simplified form of the acknowledgment signal generated by the IVC in accord with the invention.

FIGS. 9A and 9B depict COLLECT and acknowledgment signals encoded in accordance with one practice of the invention. In accord with the encoding process, referred to herein as Digital Time Segment Modulation (DTSM), the carrier signal is present at substantially all times during the transmitter ON state, with brief intervals or gaps 160–163 inserted between digital time segments 164–167. The temporal position of each gap, which defines the length of each digital time segment, is a quantity representative of digital data. In particular, as depicted in FIG. 9, the position of each gap defines bit cells indicative of encoded information.

In the illustrated embodiment, the T2 transmitter emits a carrier signal at 915 MHz, and the acknowledgment signal is transmitted at 46 MHz. Those skilled in the art will appreciate, however, that the DTSM method can be utilized to encode information in electromagnetic signals of arbitrary wavelength or frequency.

As depicted in FIG. 9A, a typical transmitted signal includes a RECEIVER-ADJUST portion 170 during which the receiver adjusts to transmitted signal amplitude; a SYNC or synchronization portion 172 enabling synchronism between receiver and transmitted signal; and a MESSAGE portion 174. The message portion can contain a MESSAGE ASSURANCE portion 176, which includes at least one parity bit or checksum bit, for checking the accuracy of the message in accordance with conventional error checking practice.

The communications event typically includes the following operations:

1. The controller module for the toll facility (FIGS. 1, 2, and 6) receives a VEHICLE-PRESENT signal from the vehicle detector, indicating the presence of a vehicle in the corresponding lane.

2. The controller module for the toll facility activates the T2 transmitter.

3. The T2 transmitter emits an RF TOLL-COLLECT signal encoded in the manner described above and depicted in FIG. 9A.

4. The IVC receives the TOLL-COLLECT signal, debits the appropriate account, and transmits an acknowledgment signal (FIG. 9B) encoded in a similar manner, with gaps 180, 181 inserted between digital time segments 182, 183. The acknowledgment signal can be frequency modulated or amplitude modulated.

5. The toll facility receives the acknowledgment signal and energizes an appropriate signal light in the enforcement light column (FIG. 6).

The DTSM encoding system provides significant advantages over conventional phase, amplitude, or frequency modulation encoding. The carrier signal is present at substantially all times during the transmitter ON state, resulting in high average signal power, and enabling the use of a simple, moderate-sensitivity, low-cost receiver in the IVC to acquire the peak incoming signal. Additionally, the encoding provides a signal in which the data portion has a fixed, known location. The encoding also provides the receiver an extended opportunity to acquire the signal before transmission of the data portion. Moreover, the encoded signal is readily decoded, using conventional digital techniques.

In one embodiment of the invention, the starting position of the acknowledgment message is varied, based upon the time at which TOLL-COLLECT signal is transmitted, as well as upon the contents of the COLLECT signal. Additionally, to reduce the potential for unauthorized recording and reproduction of the acknowledgment signal, the TOLL-COLLECT message is not a fixed message. It is selected from a set of TOLL-COLLECT messages, each of which is recognized by the IVC as a TOLL-COLLECT message. Because the COLLECT message varies over time, and the acknowledgment signal depends upon the time and content of the COLLECT message, the required acknowledgment must also vary over time, so that a previously recorded acknowledgment is unlikely to be valid at a subsequent time.

The encoding system can also insert ancillary machine readable information and user-readable information, including spoken road condition reports for motorists or encoded data for on-board map display devices.

In addition to the foregoing specific embodiments of an automated toll collection system, the invention contemplates systems wherein the distribution of processing and accounting data between the IVC and the T2/central system contains further, or dynamically changing information, yet allows transactions to be effectively completed in short times and with minimal possibility of system abuse or data error.

In one such system, indicated in FIG. 2A, the schedule of vehicle tolls described above is transmitted not by the exit identifying transmitter T1, but by each entrance transmitter T0. When toll schedule information is provided to the IVC in this manner, each transmitter T0 need not transmit a full matrix of toll amounts for all entries and exits, but needs only to transmit the toll schedule for vehicles entering the particular fixed entry at which that T0 is located. Thus, for example, where a progressive toll schedule depends on entry point, exit point and vehicle class, then rather than a three-dimensional toll schedule matrix, T0 transmits the entry identifier and a two-dimensional toll matrix arranged by vehicle class and exit numbers. The IVC then receives and stores so much of the table as is relevant to it. It is contemplated that each IVC will be issued for a fixed vehicle class (e.g., 2-axle private vehicle, 3-axle commercial vehicle under 10 tons weight, etc.), so as the vehicle passes an entry transmitter T0 it receives the transmitted schedule and stores a simple one-line table of tolls corresponding to the toll at each exit for vehicles of its own vehicle class, arranged by exit number. The device can be arranged, if desired, to store all of the information it receives.

Thus, as the vehicle enters the roadway it acquires all information it needs for subsequent toll payment. In particular, the step of checking that its account maintains an adequate balance may also be done at any time after this entry point, rather than in the environs of T1 at its intended exit point, where the traffic and the RF signal environment are each more congested and likely to cause error or delay.

As will be described in greater detail below, a preferred embodiment of the invention distributes greater "intelligence" to the in vehicle components, making them more active repositories of billing and accounting information, rather than passive toll-payers. In a toll system wherein toll surcharges are imposed based upon time-of-day at entry or exit, the IVC processor may include a processing program which implements such surcharge. In that case, the entrance transmitter T0 or the exit transmitter T1 may also broadcast the current time.

In accordance with one such further aspect of the invention, the IVC is configured such that its account balances are maintained as a programmed minimum balance debit card. Briefly, the software 53 (FIG. 3) implements algorithms to check the account balance against a programmed minimum balance level, which is preferably an amount such as twenty or thirty dollars, rather than against the toll presently due at an exit, or the maximum roadway toll which might be due according to the schedule broadcast at the entry. If the balance has dropped below the programmed minimum level the processor 50 "tops up" the balance by incrementing the balance maintained in storage by an authorized fixed increment (e.g., ten or twenty dollars), and sets an ACCOUNT INCREMENTED flag, which, as described further below, is accessed during a subsequent communication so that the central data system can bill the user for the top up charges via an external and independent billing system, such as a credit card or telephone billing system. It is also possible to configure the IVC to increment the deficiency necessary to attain the required minimum balance, but this is not preferred since it would result in a separate billing to "refill" the card every time a toll is paid.

An illustrative embodiment of this aspect of the system is implemented as follows. When the IVC is originally provided to the user, the user pays to acquire an initial balance, e.g., fifty dollars, and selects from one of several available "minimum balance" levels (e.g., twenty or thirty dollars) and also executes an authorization for billing, to a specific credit card number, telephone account, bank account or the like, any account transactions which are undertaken to maintain the minimum level. The authorization instructs the IVC to top up the account by a fixed increment, e.g., twenty dollars, when the balance drops to or below the minimum. This authorized billing information becomes part of the user's file in the central data system, while the threshold lower balance and the increment amount are entered in appropriate program instructions in the non-volatile memory 52 of the IVC. Software 53 then implements the balance check as described above against the designated threshold. If the balance remaining after payment of a toll has dropped below the threshold, then, rather than signaling the user to initiate a financial transaction at payment station 17 as described in respect to the first embodiment above, the IVC simply increments the balance internally and creates a record of the transaction, e.g., sets a BALANCE INCREMENTED flag. This transaction information is then accessed by the processor 50 and as discussed further below, is included in the next outgoing communication by the IVC transponder.

In a most preferred embodiment of this aspect of the invention, this is accomplished as follows. After receiving the exit or toll station identifier from T1 as the vehicle approaches an exit or toll station, the IVC processor 50 retrieves the toll amount from its stored toll schedule and debits the balance. It then checks the remaining balance against the designated minimum, and having checked its balances and determined them to be below the threshold, increments the balance by twenty dollars and sets the BALANCE INCREMENTED flag. It then sends a message to the toll station receiver, receives an acknowledgment as it passes the station, and stores the debited balance in non-volatile memory. The data transmitted by the IVC at each toll collection site include three pieces of information, namely 1. an IVC identification number,
2. the toll it pays at that site, and
3. the account balance.

Optionally other information, such as an indication of the last entry point, the time of entry, or other information which allows the toll station to confirm the formal correctness of the message, or allows the TTM to verify the accounting may also form part of the basic message passed to the toll station receiver. The IVC identifier preferably includes code bits indicating the vehicle class as well as the individual identification number, and the account balance report as discussed above includes code bits or information signifying that the balance has been incremented since the last use, if that is the case. This transmitted information suffices for the toll collection terminals at the exits to perform double entry bookkeeping and generate appropriate electronic or printed billing transaction records, as follows.

When the RF receiver/reader 24 at a toll site receives the vehicle toll transaction report from an IVC, it sends an acknowledgment to the IVC, which completes its transaction processing and returns to a hibernation state. Provided the IVC has transmitted an identification, toll and balance, it is presumed valid and allowed to pass. The toll station receiver, however, also provides the information received in the IVC report to the toll transaction module 32 which retrieves the financial record for the identified IVC and compares the received balance and toll paid with the last recorded balance for that identification number as it appears in the system central information records. If there is a discrepancy between the IVC-reported balance and the central record balances, and the BALANCE INCREMENTED bits have been transmitted, the TTM generates a financial transaction record for the increment. This record is used, at that time or later, to update the central account records and produce a record of the amount of the increment that is billed to the creditor account (bank, credit card or telephone billing account) which has been previously designated and authorized by the user. Otherwise, that is if there is a balance discrepancy but the BALANCE INCREMENTED bits do not appear in the received message, then this is taken as an indication of either user misconduct such as tampering, or a malfunction or error in the IVC or central records which will require inspection of the records and a bookkeeping rectification. In such case an ERROR/INVALID record is generated, and this is entered into the central system records together with the other received vehicle exit toll record data for that IVC.

When an ERROR/INVALID message is sent to the central records based on detection of anomalous balances of an IVC, the IVC identification number is added to a central list of invalid IVCs. This INVALID IVC list corresponds roughly to commonly used lists, such as the listing of lost, stolen, revoked or suspended credit cards promulgated to retailers by a credit card company. As with such lists, the INVALID IVC list contains the identity of each IVC that has been determined to be presently invalid, either because of an anomalous balance figure that requires inspection or correction as just described, or because the user did not pay or has had revoked the account to which the IVC minimum balance increments were to be charged, or because the IVC itself has otherwise been determined to be lost, stolen or involved in fraudulent toll or unauthorized transactions (such as the use of an IVC in a vehicle of a heavier class to avoid paying the higher toll schedule).

The INVALID IVC list is preferably enforced as follows to assure that an identified IVC is not repeatedly used to evade tolls. As described above, at each toll station or exit, a transmitter T1 broadcasts the identity of that toll station. In the system having an INVALID IVC list as just described, transmitter T1 receives a copy of this list and broadcasts it also. That is, T1 broadcasts a complete listing of the invalid IVCs, preferably as a continuous sequence of IVC identification numbers. It will be recalled that transmitter T1 is located ahead of the toll station, and has a range of approximately one mile, so that its transmissions will be received by a highway vehicle during a time interval generally of one-half to two minutes. It is contemplated that the IVC list will contain several to several hundred IVC identification numbers, and its transmission would therefore take only a fraction of a second at a typical 9600 baud transmission rate.

The transmitted IVC numbers are received and demodulated by the receiver section 60 of the IVC in each approaching vehicle, and the invalid IVC identification numbers are passed through a shift register which clocks out the successive IVC numbers as output words. The bits of each output word of this-register are coupled to one input of each gate of a multi-gate comparator array, each of the other inputs fixedly receiving a corresponding bit of the IVC's own identification number. When a number on the invalid IVC list matches that of the vehicle IVC identification number, the output of the comparator array goes high. This signal in turn actuates a switch that turns the IVC transmitter 56 off. In this manner, the transponder portion of the IVC is disabled as the vehicle approaches within one mile of the toll station. This assures that the IVC cannot transmit to the toll station or transact any further automated payments. Simultaneously with shut down of the IVC transmitter, an in-vehicle alarm—such as a beeper and blinking red light alarm—is activated to directly warn the driver that the IVC is inoperative and the vehicle must stop at a manual payment station.

In further or alternative embodiments of this aspect of the invention, rather than turning off the IVC transmitter and relying on user compliance or additional systems for identification of toll violators and ultimate enforcement, the transmitter may remain energized, and be controlled by the firmware and included software to initiate an immediate broadcast of a special OFFENDER message together with its IVC identification, rather than the usual toll/balance message. In this alternate embodiment the receivers at the toll station may then continue to receive IVC transmissions, identify the lane location of such an incoming vehicle with their narrow-field transmitters, and thus identify the precise lane in which the IVC OFFENDER vehicle is traveling. Having so identified the vehicle from an OFFENDER message received by the transmitter/receiver T2 a simple logical switch or the TTM 32 then turns on an alarm light to indicate to enforcement personnel the traffic lane in which the offending vehicle is traveling. Thus, if the vehicle attempts to proceed through the automated toll station despite its invalid account balance, the broadcast of the INVALID IVC list converts the IVC to operate as an offender-identifying beacon.

In a related embodiment of this aspect of the invention, such an OFFENDER message may be transmitted by means other than using the RF message transmitter with which communications to a toll station are effected. For example, a beacon in the form of an infrared (IR) or visible light emitter mounted adjacent to the vehicle registration tag or license plate may be activated (or inactivated) to indicate an INVALID IVC or OFFENDER status. A beacon of this type may then be recognized and recorded or otherwise policed visually, for example, by using an infrared viewer or a video camera-based enforcement system. It is contemplated that a preferred image-based enforcement system of this type would recognize valid toll payors by the presence of an illuminated IR beacon. In that case, object tracking software operating on a video camera image of the toll road traffic would identify as offenders all vehicles which lack the IR beacon or which have not at least briefly flashed an IR beacon during a recognition protocol. Such system would actuate enforcement cameras to photograph the vehicles on the roadway whenever such an offender is detected. By detecting the lack of beacon, such a system would identify and photograph those vehicles lacking an IVC altogether, as well as vehicles having an invalid IVC which has received a shut-down or OFFENDER identification message at T1.

In the foregoing description, the various toll station arrangements (progressive or fixed toll roads) have been described in configurations common on highway systems of the northeastern United States. Another common arrangement involves a more or less continuous sequence of toll stations appearing at intervals of every five to twenty-five miles. In this latter sort of toll road, there may be several entrance roads located between a pair of successive toll stations, but the toll charged need not vary with the vehicle entry point. Instead, when a vehicle passes through a toll station, it pays a fixed toll irrespective of when it first entered the road. Such toll stations need not be located at exits, but may be, and generally are, situated between exits, or just before entrances.

When used in a system having only such a toll arrangement, the IVC software 52 need not keep track of the vehicle entry point; a toll schedule broadcast at each T1 may be a single amount; and the toll station need not have a number or other identifier. In this case, the role of transmitter T0 is superfluous, and the data transmitted by T1 is correspondingly reduced. When intended for such a toll system, the transaction report sent by the IVC, however still includes the identification and balance information described above.

It will be further appreciated that rather than a set of toll booths with blocking gates or turnstiles, the automated toll stations described above require no structures on the road itself, and may physically be implemented with a single gantry extending over all lanes of the road. In this case, on top of the gantry are mounted the narrow beam toll station transmitters and receivers to receive toll payment communications. Preferably these receiver/transmitters also actuate lane-indicator lights facing downstream of the traffic flow to visibly indicate the validity and optionally also the toll class for the toll payment of each vehicle passing thereunder.

Figure 10:
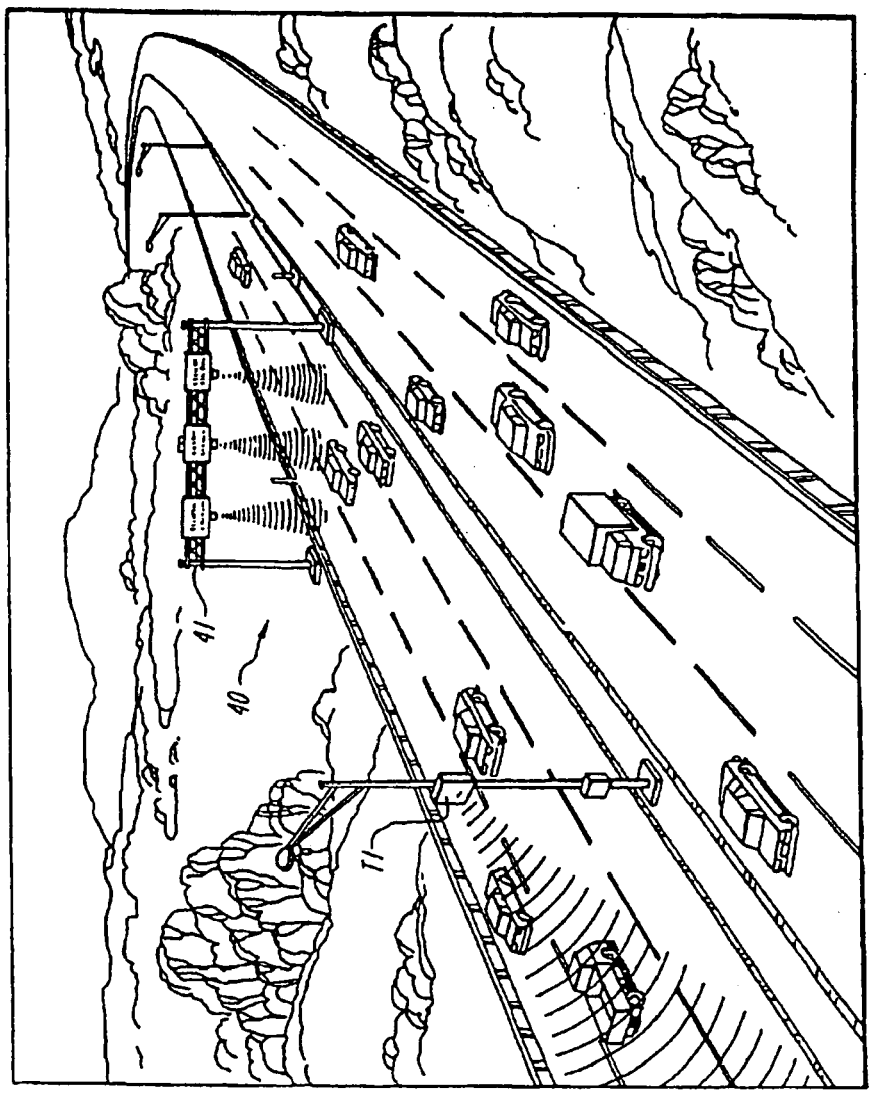
FIGS. 10, 10A show a gantry-type toll system embodiment of the invention and enforcement cameras on the gantry.
Figure 10A:
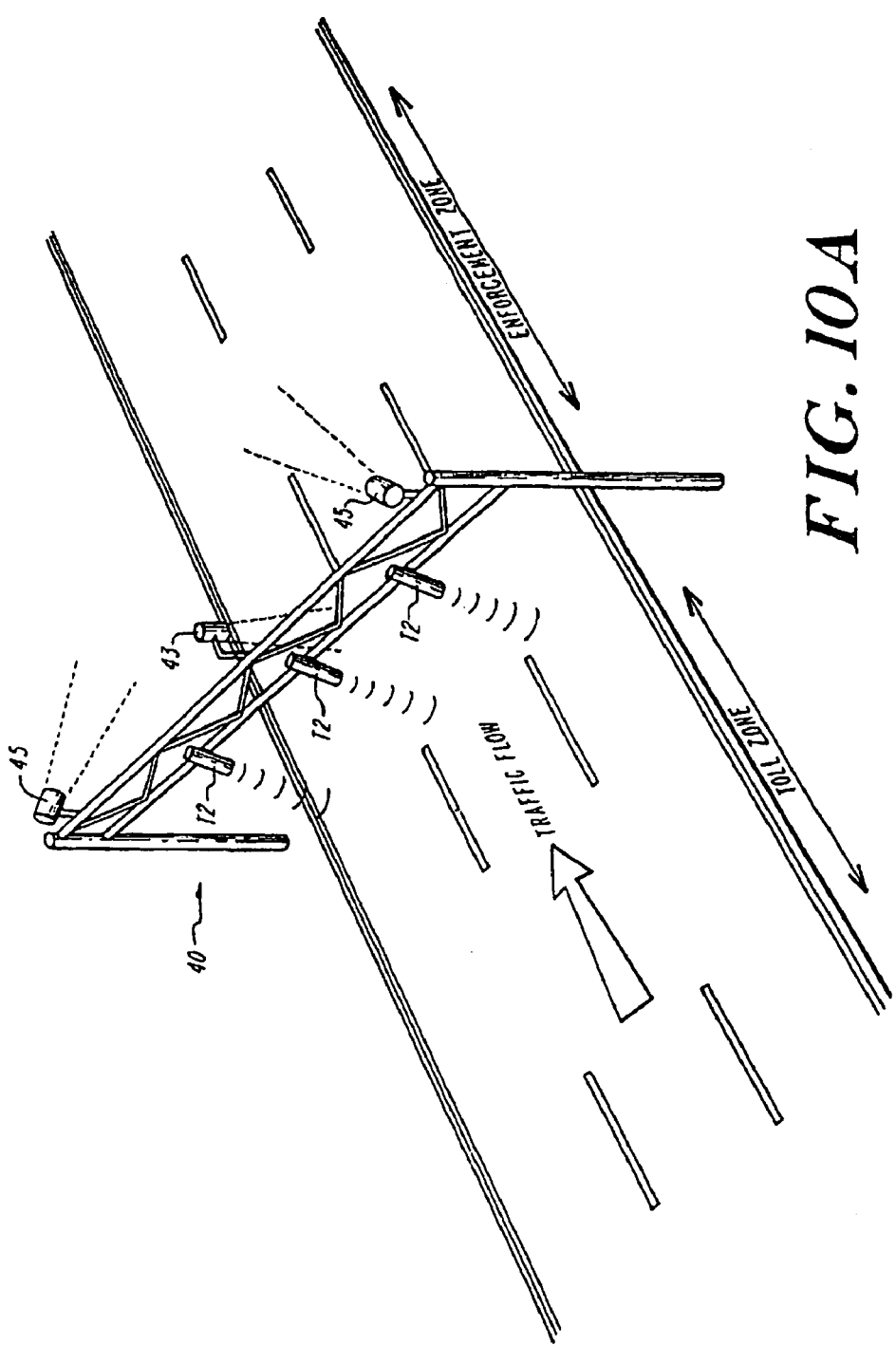

FIG. 10 illustrates such a gantry system 40, in which a support frame 41 located downstream of an identifying transmitter T1 carries a plurality of narrow beam lane identifying transmitters which each handle toll transactions with cars passing thereunder. Optionally, video enforce cameras may also be held on the gantry. In that case, one camera 43 (FIG. 10A) may be aimed essentially vertically to resolve the instantaneous position of each car passing by, while other cameras 45 may be aimed downstream to record license numbers of offenders in multiple lanes.

It will thus be seen that the invention efficiently attains the objects set forth above, among those made apparent from the preceding description. In particular, the invention provides methods and apparatus for remote, high-speed extraction of tolls from vehicles moving at high speeds. The invention thereby enables high levels of throughput that are unattainable by conventional toll collection systems. The system facilitates interaction with toll authorities, and enables efficient, low-cost record-keeping and transaction reporting for vehicle operators and toll facilities. The invention enhances highway safety by reducing speed differentials in the vicinity of toll plazas, and is readily integrated into existing toll management systems.

It will be understood that changes may be made in the above construction and in the foregoing sequences of operation without departing from the scope of the invention. The illustrated radio frequency transmitters, for example, may be replaced by transmitters or emitters operating in other regions of the electromagnetic spectrum. Moreover, the invention can be practiced in connection with railway vehicles or other toll- or tariff-collection applications.

It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall there between.

Having described the invention, what is claimed as new and secured by Letters Patent is:

1. A method for locating a mobile transceiver comprising the steps of:
   transmitting a first electromagnetic signal carrying identification information from each of a plurality of stationary transmitters in each of a plurality of respective regions wherein at least two of the regions overlap; and
   identifying a closest one of said plurality of stationary transmitters and thereafter transmitting a second electromagnetic signal from the mobile transceiver at a substantially different frequency than that of the first electromagnetic signal, which second electromagnetic signal indicates the identity of the closest transmitter to the mobile transceiver.

2. An apparatus for locating a mobile transceiver comprising:
   a plurality of stationary transmitters, each of said stationary transmitters transmitting a first electromagnetic signal carrying identification information in each of a plurality of respective regions wherein at least two of the regions overlap; and
   a mobile transceiver having a preassigned identity and including a transmitter, a receiver, and a processor, the mobile transceiver identifying a closest one of said plurality of stationary transmitters and thereafter transmitting a second electromagnetic signal at a substantially different frequency than that of the first electromagnetic signal, which second electromagnetic signal indicates the identity of the closest transmitter to the mobile transceiver.

3. The method of claim 1, wherein the step of transmitting a first electromagnetic signal carrying identification information from each of a plurality of stationary transmitters in each of a plurality of respective regions wherein at least two of the regions overlap, comprises:
   transmitting a first electromagnetic signal carrying identification information from each of a plurality of stationary transmitters in each of a plurality of respective regions, each of the plurality of respective regions covering at least a respectively different lane of a multi-lane road, wherein at least two of the regions overlap.

4. The apparatus of claim 2, wherein each of said plurality of respective regions covers at least a respectively different lane of a multi-lane road; and
   wherein at least two of the regions overlap.

* * * * *